United States Patent
Ghosal et al.

(10) Patent No.: US 10,449,206 B2
(45) Date of Patent: Oct. 22, 2019

(54) INDOLEALKYLAMINO-WITHASTEROID CONJUGATES AND METHOD OF USE

(71) Applicant: Natreon, Inc., New Brunswick, NJ (US)

(72) Inventors: Shibnath Ghosal, Kolkata (IN); Muruganandam Veeraragavan, Kolkata (IN); Sanyasi R. Kalidindi, Monroe, NJ (US)

(73) Assignee: Natreon, Inc., New Brunswick, NJ (US)

( * ) Notice: Subject to any disclaimer, the term of this patent is extended or adjusted under 35 U.S.C. 154(b) by 354 days.

(21) Appl. No.: 14/805,024

(22) Filed: Jul. 21, 2015

(65) Prior Publication Data

US 2015/0320771 A1  Nov. 12, 2015

Related U.S. Application Data

(62) Division of application No. 13/669,207, filed on Nov. 5, 2012, now Pat. No. 9,084,800.

(60) Provisional application No. 61/556,603, filed on Nov. 7, 2011.

(51) Int. Cl.

| | |
|---|---|
| *A61K 36/00* | (2006.01) |
| *A61K 36/81* | (2006.01) |
| *A61K 31/585* | (2006.01) |
| *A61K 36/38* | (2006.01) |
| *C07J 71/00* | (2006.01) |
| *A61K 47/54* | (2017.01) |

(52) U.S. Cl.
CPC ............ *A61K 31/585* (2013.01); *A61K 36/38* (2013.01); *A61K 47/541* (2017.08); *A61K 47/545* (2017.08); *C07J 71/001* (2013.01)

(58) Field of Classification Search
None
See application file for complete search history.

(56) References Cited

U.S. PATENT DOCUMENTS

| | | | |
|---|---|---|---|
| 5,403,851 A | 4/1995 | D'Orlando et al. | |
| 6,153,198 A | 11/2000 | Ghosal | |
| 2004/0166184 A1 | 8/2004 | Ghosal | |
| 2004/0253647 A1* | 12/2004 | Mathews | G01N 33/5008 435/7.2 |
| 2005/0266100 A1* | 12/2005 | Sangwan | A61K 36/81 424/725 |
| 2010/0120747 A1 | 5/2010 | Codony-Soler et al. | |
| 2011/0230551 A1 | 9/2011 | Gunatilaka et al. | |

FOREIGN PATENT DOCUMENTS

| | | |
|---|---|---|
| EP | 2 260 855 A1 | 12/2010 |
| EP | 2260855 A1 | 12/2013 |
| WO | 2004050015 A2 | 6/2004 |
| WO | 2007014334 A2 | 2/2007 |

OTHER PUBLICATIONS

Vickers (A Vaccine Against Alzheimer's Disease, Drug Aging 2002: 19(2) 487-494).*
Archana, R., et al., Antistressor effect of Withania somnifera, Journal of Ethnopharmacology (1999) 64: 91-93.
Bhattacharya, S.K., et al., Anti-Stress Activity of Sitoindosides VII and VIII, New Acylsterylglucosides from Withania Somnifera, Phytotherapy Res. (1987) 1(1): 32-37.
Bhattacharya, S.K., et al., Effects of Glycowithanolides from Withania somnifera on an Animal Model of Alzheimer's Disease and Perturbed Central Cholinergic Markers of Cognition in Rats, Phytotherapy Res. (1995) 9: 110-113.
Bhattacharya, S.K., et al., Anxiolytic-antidepressant activity of Withania somnifera glycowithanolides: an experimental study, Phytomedicine (2000) 7(6): 463-469.
Bhattacharya, S.K., et al., Adaptogenic activity of Withania somnifera: an experimental study using a rat model of chronic stress, Pharmacol. Biochem. Behav. (2003) 75(3): 547-555. (Abstract Only).
Glotter, E., Withanolides and Related Ergostane-type Steroids, Nat. Prod. Rep. (1991) 8: 415-440.
International Search Report of International Appl. No. PCT/US12/63727, Form PCT/ISA/210, Second sheet, dated Jan. 23, 2013.
Jayaprakasam, B., et al., Withanamides in Withania somnifera Fruit Protect PC-12 Cells from β-Amyloid Responsible for Alzheimer's Disease, Phytotherapy Res. (2010) 24: 859-863.
Mirjalili, M.H., et al., Steroidal Lactones from *Withania somnifera*, an Ancient Plant for Novel Medicine, Molecules (2009) 14: 2373-2393.
Mishra, L-C., et al., Scientific Basis for the Therapeutic Use of *Withania somnifera* (Ashwagandha): A Review, Alt. Medicine Rev. (2000) 5(4): 334-346.
Misra, L., et al., "Selective reactivity of 2-mercaptoethanol with 5beta, 6beta-epoxide in steroids from Withania somnifera," Steroids (2008) 73(3):245-251.

(Continued)

*Primary Examiner* — Michael Barker
*Assistant Examiner* — Randall Winston
(74) *Attorney, Agent, or Firm* — Amin Talati Wasserman; George M. Carrera, Jr.

(57) ABSTRACT

A group of indolealkylamino-withasteroid conjugates, isolated and purified from *Withania somnifera*, are described. A synthetic method of making an indolealkylamino-withasteroid compound is provided. In vitro acetyl cholinesterase inhibitory activity and methods for treatment of dementia and dementia-related disorders, such as Alzheimer's disease, and anxiety and depressive disorders in mammals are demonstrated with these novel compositions.

4 Claims, 5 Drawing Sheets

(56) References Cited

OTHER PUBLICATIONS

Vaidya, A.D.B., The Status and Scope of Indian Medicinal Plants Acting on Central nervous System, Indian J. Pharmacol. (1997) 29: S340-S343.
National Biodiversity Authority, Government of India, The Biological Diversity Act, 2002.†

\* cited by examiner
† cited by third party

Scheme 1

INDOLEALKYLAMINO-WITHASTEROID CONJUGATES AND METHOD OF USE

This application is a divisional of U.S. patent application Ser. No. 13/669,207, filed Nov. 5, 2012, now issued as U.S. Pat. No. 9,084,800, which claims the benefit of earlier filed U.S. Provisional Application No. 61/556,603, filed on Nov. 7, 2011, each of which are hereby incorporated by reference herein.

FIELD OF THE INVENTION

The present invention relates to a group of indolealkylamino-withasteroid conjugates, isolated from *Withania somnifera* and purified. This invention further relates to use of said compounds for treatment of dementia and dementia-related disorders, such as Alzheimer's disease, and anxiety and depressive disorders in a patient.

BACKGROUND

*Withania somnifera* Dunal (WS) of family Solanaceae, known as *Ashwagandha* in *Ayurveda*, the ancient Hindu system of medicine, has been in use for more than 2500 years. The roots of the plant were used in *rasayana* formulations, a group of plant-derived drugs that are reputed to promote health and longevity by augmenting body's defense mechanisms against disease, arresting the aging process, revitalizing the body in debilitated conditions, increasing the capability of the individual to resist adverse environmental factors and creating a sense of mental well-being. M. A. Weiner, J. Weiner, *Ashwagandha* (Indian Ginseng), pp. 70-72, Herbs that Heal (Mill Valley, Calif.: Quantum Books, 1994).

Several earlier investigations have indicated that WS has a profile of activity that is consonant with putative anti-stress and antioxidant activity. WS, or its major active principles, have anti-inflammatory activity, antitumor and radio-sensitizing actions and have annulled cyclophosphamide toxicity. Likewise, the active principles of WS, comprising sitoindosides VII-X and withaferin-A, have been shown to have significant antistress activity against acute and chronic models of experimental stress, immunomodulatory actions, inhibition of cognitive deficits in animal models of Alzheimer's disease, antioxidant activity in rat brain areas, and anxiolytic-antidepressant action in rats (S. K. Bhattacharya, et al., "Antistress activities of sitoindosides VII and VIII, new acyl sterylglucosides from *Withania somnifera*," *Phytother. Res.* (1987) 1:32-37; S. K. Bhattacharya, Muruganandam A. V., "Adaptogenic activity of *Withania somnifera*: an experimental study using a rat model of chronic stress," *Pharmacol Biochem. and Behavior* (2003) 75: 547-555; S. Ghosal, et al., "Immunomodulatory and CNS effects of sitoindosides IX and X, two new glycowithanolides from *Withania somnifera*," *Phytother. Res.* (1989) 3: 201-206; S. K. Bhattacharya, et al., "Effect of Trasina, an Ayurvedic herbal formulation on experimental models of Alzheimer's disease and central cholinergic markers in rats," *J. Altern. Complement. Med.* (1997) 3:327-336; S. K. Bhattacharya, et al., "Antioxidant activity of glycowithanolides from *Withania somnifera*," *Indian J. Exp. Biol.* (1997) 35: 236-239; and S. K. Bhattacharya, et al., "Anxiolytic-antidepressant activity of *Withania somnifera* glycowithanolides: an experimental study," *Phytomed.* (2000) 7: 463-469). WS root extract and its constituents, withanolides and withanosides, were also reported to possess anti-acetylcholinesterase activity and dementia thwarting activity (M. I. Choudhary, et al. "Withanolides, a new class of natural cholinesterase inhibitors with calcium antagonistic properties," *Biochem. and Biophys. Res. Comm.* (2005) 334: 276-287).

Although significant numbers of studies have been carried out on WS and its bioactives, many of them are centered on withasteroids, namely, withanolides and their glycosides. Recently, a new class of compounds, withanamides, from the fruit of WS, having antioxidant, anti-inflammatory and β-amyloid protecting activities were reported (B. Jayaprakasam et al., "Potent lipid peroxidation inhibitors from *Withania somnifera* fruits," *Tetrahedron* (2004) 60: 3109-3121; and B. Jayaprakasam et al., "Withanamides in *Withania somnifera* fruit protect PC-12 cells from beta-amyloid responsible for Alzheimer's disease," *Phytother. Res.* (2010) 24:859-63). Acetylcholinesterase inhibitors (AChEIs) are an important class of compounds which are indicated for the management of mild to moderate Alzheimer's dementia. Alzheimer's disease is associated with significant losses in cholinergic neurons and decreased concentrations of the neurotransmitter, acetylcholine, which is significantly involved in learning and memory processes. AChEIs exert pharmacologic effects by increasing availability of intrasynaptic acetylcholine in the presence of intact cholinergic neurons. There are a few synthetic medicines, e.g., Tacrine, Donepezil, Galantamine, and the natural product-based Rivastigmine that are currently being used for treatment of cognitive dysfunction and memory loss associated with Alzheimer's disease. These compounds, however, are not free from certain adverse effects including gastrointestinal disturbances and problems associated with bioavailability. The clinical usefulness of AChEIs has been limited by either an extremely short or an excessively long half-life, hepatotoxicity, and severe peripheral cholinergic side effects.

Two studies reported on the AChE activity of WS, although they were confined to the total extract and withanolides only. (M. I. Choudhary, et al., "Withanolides, a new class of natural cholinesterase inhibitors with calcium antagonistic properties," *Biochemical and Biophysical Res. Comm.* (2005) 334: 276-287; and S. Khattak, et al., "In vitro enzyme inhibition activities of crude ethanolic extracts derived from medicinal plants of Pakistan," *Nat. Prod. Res.* (2005) 19:567-571.)

WS was shown to possess learning and memory improvement activity in various animal models by different investigators. One study investigated the active principles of WS, consisting of equimolar amounts of sitoindosides VII-X and withaferin A, for putative nootropic activity in an experimentally validated Alzheimer's disease model. The syndrome was induced by ibotenic acid lesioning of the nucleus basalis magnocellularis (NBM) in rats. WS significantly reversed both ibotenic acid-induced cognitive deficits and the reduction in cholinergic markers after 2 weeks of treatment. The findings validate the medharasayan (promoter of learning and memory) effect of WS, as has been reported in *Ayurveda*. (S. K. Bhattacharya, et al., "Effects of glycowithanolides from *Withania somnifera* on an animal model of Alzheimer's disease and perturbed central cholinergic markers of cognition in rats," *Phytother. Res.* (1995) 9: 110-113.)

In another study, sitoindosides VII-X, and withaferin-A, were isolated from aqueous methanol extract from the roots of cultivated varieties of WS to attenuate cerebral functional deficits, including amnesia, in geriatric patients. Systemic application of the defined extract from WS, however, led to differential effects on AChE activity in basal forebrain nuclei; slightly enhanced AChE activity was found in the lateral septum and globus pallidus, whereas in the vertical diagonal band AChE activity was reduced following treatment with sitoindosides VII-X and withaferin-A. These changes were accompanied by enhanced M1-muscarinic cholinergic receptor binding in lateral and medial septum as well as in frontal cortices, whereas the M2-muscarinic receptor binding sites were increased in a number of cortical regions including cingulate, frontal, piriform, parietal and retrosplenial cortex. Treatment with the defined extract from WS affected neither GABA and benzodiazepine receptor binding nor NMDA and AMPA glutamate receptor subtypes in any of the cortical or subcortical regions studied. The data suggest that the defined extract from WS affect preferentially events in the cortical and basal forebrain cholinergic signal transduction cascade. The drug-induced increase in cortical muscarinic acetylcholine receptor capacity might partly explain the cognition-enhancing and memory-improving effects of extracts from WS observed in animals and humans. (R. Schliebs, et al., "Systemic administration of defined extracts from *Withania somnifera* (Indian Ginseng) and Shilajit differentially affects cholinergic but not glutamatergic and GABAergic markers in rat brain," *Neurochem. Int.* (1997) 30:181-190.)

The anxiolytic and the anti-depressant effects of glycowithanolides from WS were compared with those elicited by the anti-anxiety drug Lorazepam and by the antidepressant, Imipramine. Glycowithanolides induced an anxiolytic effect, comparable to that produced by Lorazepam, in the elevated plus-maze, social interaction, and feeding latency in an unfamiliar environment tests. Further, both the glycowithanolides and Lorazepam reduced rat brain levels of Tribulin, an endocoid marker of clinical anxiety, when the levels were increased following administration of the anxiogenic agent, pentylenetetrazole. Glycowithanolides also exhibited an antidepressant effect, comparable to that induced by Imipramine, in the forced swim-induced behavioral despair and learned helplessness tests. This investigation supports the use of WS as a mood stabilizer in clinical conditions of anxiety and depression in *Ayurveda*, and in other treatment paradigms. (S. K. Bhattacharya, et al., "Anxiolytic-antidepressant activity of WS glycowithanolides: an experimental study," *Phytomed.* (2000) 7: 463-469.)

WS root extract administration improved retention of a passive avoidance task in a step-down paradigm in mice. WS also reversed the scopolamine-induced disruption of acquisition and retention and attenuated the amnesia produced by acute treatment with electroconvulsive shock. On the elevated plus-maze, *Ashwagandha* reversed the scopolamine-induced delay in transfer latency on day 1. On the basis of these findings, it is suggested that *Ashwagandha* exhibits a nootropic-like effects in naive and amnesic mice. In another study, six compounds were isolated from the methanol extract of WS roots which enhanced neurite outgrowth in human neuroblastoma SH-SY5Y cells. That study also reported that in withanolide A-treated cells, the length of NF—H-positive process was significantly increased compared to vehicle-treated cells, whereas, the length of MAP2-positive process was increased by withanolides. (J. N. Dhuley, "Nootropic-like effect of *Ashwagandha* (WS L.) in mice," *Phytother. Res.* (2001) 15: 524-5288; and T. Kuboyama, et al., "Axon or dendrite-predominant outgrowth induced by constituents from Aswagandha," *Neuroreport.* (2002) 13: 1715-1717.)

Bhattacharya and Muruganandam A. V., cited above, investigated the adaptogenic activity of a standardized extract of WS roots against a rat model of chronic stress (CS). The stress procedure was mild, unpredictable footshock, administered once daily for 21 days to adult male Wistar rats. CS induced significant hyperglycaemia, glucose intolerance, increase in plasma corticosterone levels, gastric ulcerations, male sexual dysfunction, cognitive deficits, immunosuppression and mental depression. These CS induced perturbations were attenuated by WS extract administered 1 hour before footshock for 21 days. The results indicate that WS has significant antistress and adaptogenic activity.

It was also reported that withanolides 1-3, and 4 and 5 isolated from *Ajuga bracteosa* and WS, respectively, inhibited acetylcholinesterase and butyrylcholinesterase enzymes in a concentration-dependent fashion. It was suggested that the cholinesterase inhibitory potential along with calcium antagonistic ability and safe profile in human neutrophil viability assay could make withanolides 1-5 possible drug candidates for further study to treat Alzheimer's disease and associated problems. It was also reported that some active constituents of WS such as withanolide A, withanoside IV and withanoside VI could improve Amyloid-β (25-35)-induced memory impairment, neuronal atrophy and synaptic loss in the cerebral cortex and the hippocampus. (M. I. Choudhary, et al., "Withanolides, a new class of natural cholinesterase inhibitors with calcium antagonistic properties," *Biochem. and Biophys. Res. Comm.* (2005) 334: 276-287; and T. Chihiro, et al., "Scientific basis for the anti-dementia drugs of constituents from *Ashwagandha* (WS)," *J. Trad. Med.* (2005) 22:176-182.)

Anxiolytic and anti-depressant activities of WS root extract in social isolation induced behavior such as anxiety and depression in rats, has been reported. (G. L. Gupta, et al., "Protective Effect of WS Dunal Root Extract against Protracted Social Isolation Induced Behavior in Rats," *Indian J. Physiol. Pharmacol.* (2007) 51: 345-353.)

Oral administration of WS extract exerts protective effect and attenuates AChE inhibition and cognitive impairment caused by sub-chronic exposure to Propoxur, which blocks the production and action of acetylcholinesterase. (C. S. Yadav, et al., "Propoxur-induced acetylcholine esterase inhibition and impairment of cognitive function: attenuation by *Withania somnifera*," *Indian J. Biochem. Biophys.* (2010) 47:117-20.)

As discussed above, several bioactive principles of WS have been isolated and their antioxidant, anti-stess, anxiolytic and anti-cholinesterase activities have been extensively studied. The drugs commonly used as anxiolytics, for example the benzodiazepines, and drugs used for treating Alzheimer's disease can have severe side effects. Thus there is a need and a desire for a better class of drugs without adverse side effects. The present invention describes the isolation, purification, and pharmacological actions of a novel group of drugs, namely indolealkylamino-withasteroid conjugates, from WS. It is, however, possible that these novel compounds may be obtained from other plants as well.

In view of the above, it would be desirable to provide a potent and therapeutically effective extract of WS in a pharmaceutical or nutraceutical composition having improved properties for the treatment or prevention of ailments, in particular, neurological deficiencies and depression. It would also be desirable to provide an extract of WS for use as a nutritional supplement.

If a way could be found to enhance or enrich the levels of withanolides and/or withasteroids in a WS extract, this would represent a valuable contribution to the art.

SUMMARY OF THE INVENTION

In one embodiment, the present invention relates to a group of novel indolealkylamino-withasteroid conjugates, isolated and purified from *Withania somnifera* (WS), and their use in the treatment of dementia and dementia-related diseases, such as Alzheimer's disease, and anxiety and depressive disorders in mammals. These novel indolealkylamino-withasteroid conjugates or compounds have the general structural formulae of Formula (I):

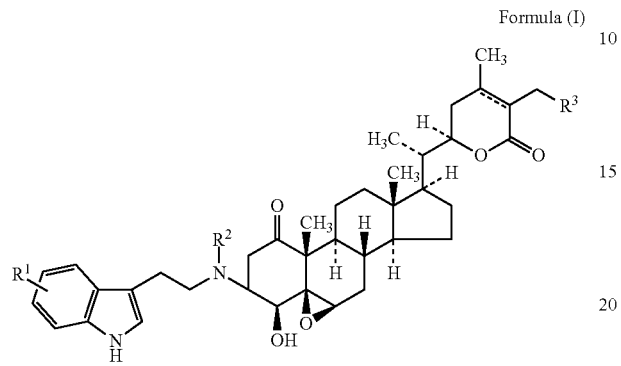

Formula (I)

wherein $R^1$ is selected from the group consisting of hydrogen, hydroxyl, and $(C_1-C_4)$-alkoxy;
wherein $R^2$ is hydrogen or methyl,
wherein $R^3$ is hydrogen or hydroxyl; and
wherein ----- represents a single or a double bond;
and salts thereof.

In an alternative embodiment according to formula (I), $R^1$ is selected from the group consisting of hydrogen, $(C_1-C_3)$-alkyl, hydroxyl, and $(C_1-C_4)$-alkoxy; and $R^2$ is hydrogen or $(C_1-C_3)$-alkyl.

In another embodiment, the present invention relates to compounds having the general structural formulae of Formula (I). The compounds may be prepared by chemical synthesis or semi-synthesis, and/or isolated and purified to provide compounds of Formula (I).

In one aspect, the compounds of Formula (I) are conjugates derived from withaferin A (1) and a tryptamine derivative (2).

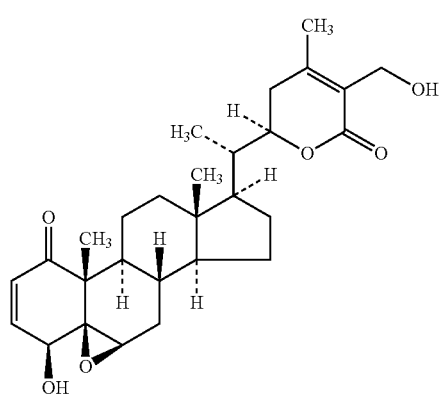

(1)

Withaferin A (aglycone) (1) is the major withanolide aglycone in WS. Withanolides are C-28 steroidal lactones of the ergostane type, and are generically named "withasteroids" herein.

Furthermore, derivatives of the withaferein-A compound (1) are contemplated having a withanolide structure (1-a)

wherein $R^3$ is hydrogen or hydroxyl; and wherein ----- represents a single or a double bond.

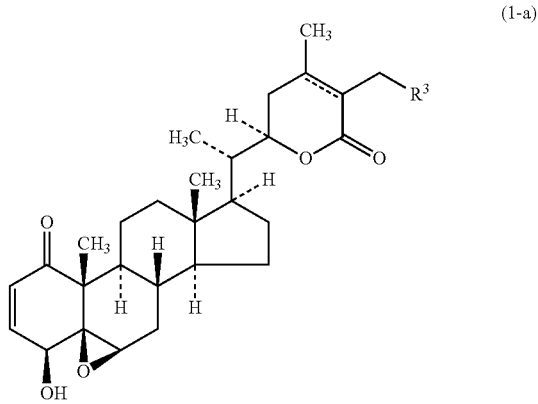

(1-a)

Therefore, the compounds of Formula (I) may be conjugates derived from a withanolide derivative (1-a) and a tryptamine derivative (2).

Tryptamines represented by structure (2) are biologically active compounds that include tryptamine ($R^1$, $R^2$=H), serotonin ($R^1$=5-hydroxy, $R^2$=H), and 5-methoxytryptamine ($R^1$=5-methoxy, $R^2$=H).

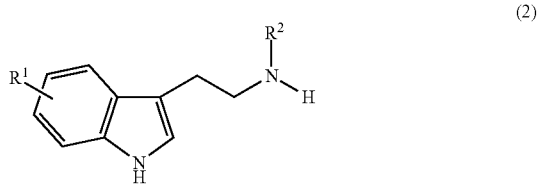

(2)

wherein $R^1$ is selected from the group consisting of hydrogen, hydroxyl, and $(C_1-C_4)$-alkoxy; and
wherein $R^2$ is hydrogen or methyl,
and salts thereof.

In an alternative embodiment according to structure (2), $R^1$ is selected from the group consisting of hydrogen, $(C_1-C_3)$-alkyl, hydroxyl, and $(C_1-C_4)$-alkoxy; and $R^2$ is hydrogen or $(C_1-C_3)$-alkyl.

An objective of the present invention is to isolate, purify and characterize indolealkylamino-withasteroid conjugates having Formula (I) from *Withania somnifera*. One or more indolealkylamino-withasteroid conjugates having Formula (I) may be contained in an extract or blend.

Another objective of the present invention is to chemically synthesize indolealkylamino-withasteroid conjugates having Formula (I).

A method of making a compound of Formula (I) can include the steps of: (a) providing a tryptamine compound or derivative having formula (2); (b) adding a solution of the tryptamine compound (2) to a withaferin-A compound (1) or a derivative thereof, such as withanolide compound (1-a); (c) optionally heating the resulting reaction mixture; and (d) isolating the compound of Formula (I), or a salt thereof.

In another embodiment, the invention relates to a method for treatment of dementia and the dementia-related disorders, e.g., Alzheimer's disease, in mammals by administering one or more isolated indolealkylamino-withasteroid conjugates having Formula (I), salts thereof, and mixtures thereof. A further embodiment of the invention relates to a method for treating dementia and the dementia-related disorders by administering to a patient in need thereof an effective amount of an extract containing one or more isolated indolealkylamino-withasteroid conjugates having Formula (I), salts thereof, and mixtures thereof.

In a still further embodiment, the invention relates to a method for treatment of anxiety disorders in mammals by administering one or more isolated indolealkylamino-withasteroid conjugates having Formula (I), salts thereof, and mixtures thereof. Yet another embodiment of the invention relates to a method for treating anxiety disorders by administering to a patient in need thereof an effective amount of an extract containing one or more isolated indolealkylamino-withasteroid conjugates having Formula (I), salts thereof, and mixtures thereof.

In yet another embodiment, the invention relates to method for treatment of depressive disorders in mammals by administering one or more isolated indolealkylamino-withasteroid conjugates having Formula (I), salts thereof, and mixtures thereof. Yet another embodiment of the invention relates to a method for treating depressive disorders by administering to a patient in need thereof an effective amount of an extract containing one or more isolated indolealkylamino-withasteroid conjugates having Formula (I), salts thereof, and mixtures thereof.

In a further embodiment, the invention relates to a pharmaceutical or nutraceutical composition containing one or more isolated indolealkylamino-withasteroid conjugates having Formula (I), salts thereof, and mixtures thereof, and a pharmaceutically acceptable carrier. In a yet further embodiment, the invention relates to a pharmaceutical or nutraceutical composition containing an extract including one or more isolated indolealkylamino-withasteroid conjugates having Formula (I), salts thereof, and mixtures thereof, and a pharmaceutically acceptable carrier.

An objective of the present invention is to develop an optimized extraction process to enrich the bioactive contents, namely, one or more isolated indolealkylamino-withasteroid conjugates having Formula (I).

DETAILED DESCRIPTION

Figure 1A:
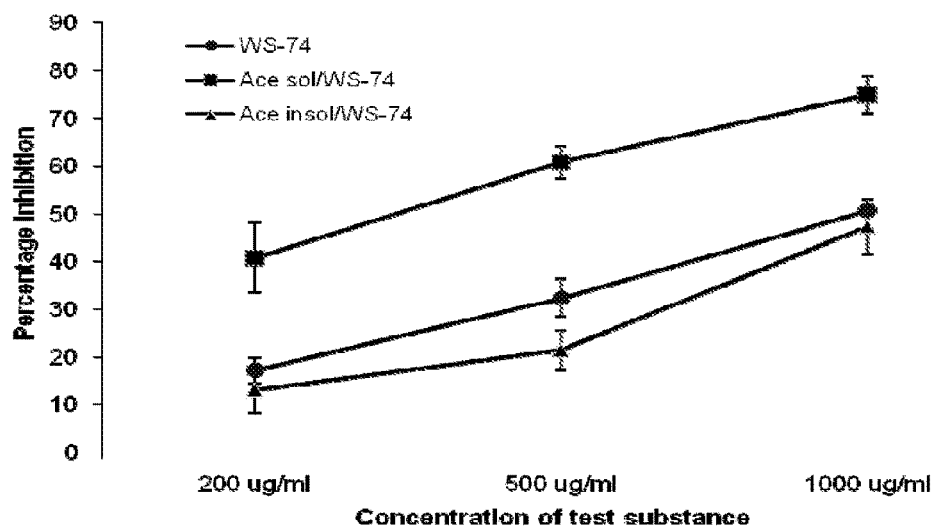
FIG. 1A depicts percent inhibition of acetylcholinesterase by test samples of *Withania somnifera* (WS) extract as a function of concentration.

In an embodiment, a *Withania somnifera* (WS) extract containing one or more isolated indolealkylamino-withasteroid conjugates having Formula (I) is provided. A method for extracting *Withania somnifera* (WS) to obtain product enriched in indolealkylamino-withasteroid conjugates having Formula (I) is also provided.

In another embodiment, the invention is directed to a compound having Formula (I), or a salt, hydrate, solvate, or prodrug thereof.

The indolealkylamino-withasteroid conjugates have the general structural formulae of Formula (I):

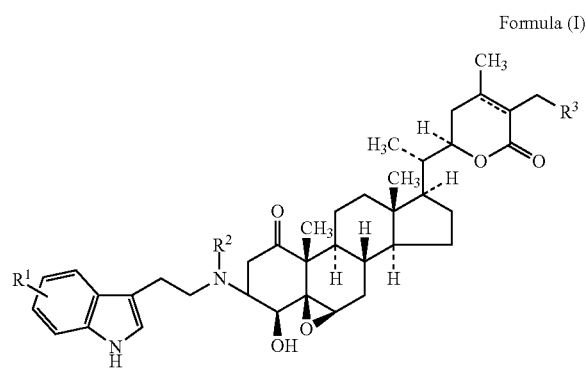

Formula (I)

wherein $R^1$ is selected from the group consisting of hydrogen, hydroxyl, and $(C_1-C_4)$-alkoxy;

wherein $R^2$ is hydrogen or methyl, wherein $R^3$ is hydrogen or hydroxyl; and wherein ═════ represents a single or a double bond;

and salts thereof.

In an alternative embodiment according to Formula (I), $R^1$ is selected from the group consisting of hydrogen, $(C_1-C_3)$-alkyl, hydroxyl, and $(C_1-C_4)$-alkoxy; and $R^2$ is hydrogen or $(C_1-C_3)$-alkyl.

In the compounds of Formula (I), the substituent group $R^1$ may be optionally positioned at any available position on the benzenoid ring of indole.

In one aspect, the compounds Formula (I) include a steroid portion based on the ergostane class, for example, withaferin A (1), which is a prototypical withanolide compound. Withanolides are C-28 steroidal lactones of the ergostane type, and are generically named "withasteroids" herein.

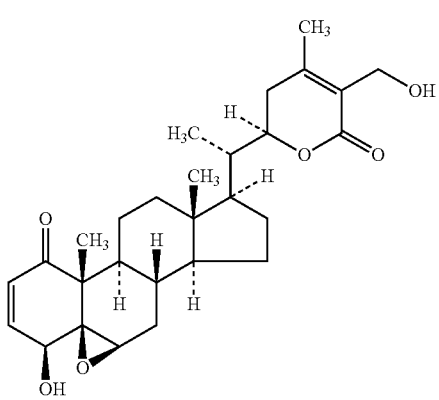

In another aspect, the compounds of Formula (I) may include a steroid portion based on the ergostane class, for example, a compound having a withanolide structure (1-a), which is a withanolide compound wherein $R^3$ is hydrogen or hydroxyl; and wherein ----- represents a single or a double bond.

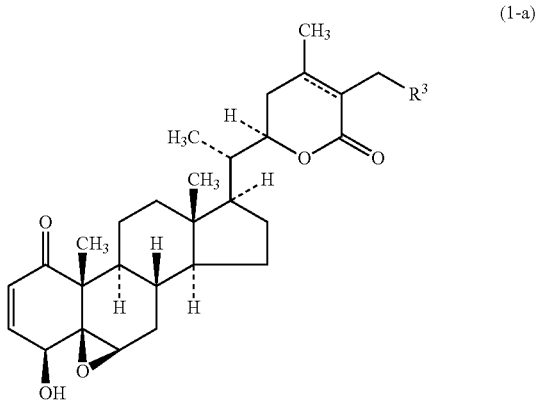

However, the present invention is not intended to be limited to the withasteroids (i.e., the steroid portion) of Formula (I), which is generally based on the structure of withaferin A (1) or the withanolide compound (1-a). Other withasteroid structures are contemplated in the embodiments of the present invention. Thus, other useful steroid moieties may include any of the withanolide class of ergostanes, as described in E. Glotter, Nat. Prod. Rep. (1991) 8:415-440, or M. H. Mirjalili, et al., Molecules (2009) 14:2373-2393, herein incorporated by reference.

Definitions

As used in the specification and the appended claims, the singular forms of "a," "an" and "the" include plural referents unless the context clearly dictates otherwise.

As used herein, the terms "treat" and "treatment" are used interchangeably and are meant to indicate a postponement of development of an ailment or disorder and/or a reduction in the severity of symptoms that will or are expected to develop. The terms further include ameliorating existing symptoms, preventing additional symptoms, and ameliorating or preventing the underlying metabolic causes of symptoms.

As used herein, the term "individual" (as in the subject of treatment, or patient) means both mammals and humans.

The expression "effective amount," when used to describe therapy to an individual suffering from a disorder, refers to the amount of a compound according to Formula (I), or an amount of a pharmaceutical composition containing at least one compound of Formula (I), that inhibits, reduces, or otherwise treats the disorder, for example, a dementia-related disorder, anxiety, or depression.

It is understood that a hashed bond mark (-----) between two carbon atoms represents either a carbon-carbon single bond or a carbon-carbon double bond, as appropriate.

The term "alkyl," by itself or as part of another substituent means, unless otherwise stated, a straight, branched or cyclic chain hydrocarbon (cycloalkyl) having the number of carbon atoms designated (i.e., $C_1$-$C_6$ means one to six carbons). Examples include methyl, ethyl, propyl, isopropyl, butyl, isobutyl, tert-butyl, pentyl, neopentyl, hexyl, cyclohexyl, and cyclopropyl. Most preferred are ($C_1$-$C_3$)-alkyl, particularly ethyl, methyl and isopropyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)-alkoxy, particularly methoxy and ethoxy.

As used herein, the term "semi-synthesis" refers to a chemical processes that employs a naturally-derived starting material or compound, and/or employs a naturally derived process, such as enzymatic catalysis, for example. A "semi-synthetic" compound is defined as a compound of which part of the structure has been isolated from natural (including botanical and herbal) sources, and part of the structure has been synthesized.

Synthetic preparation of Indolealkylamino-withasteroid conjugate compounds.

In one embodiment, a method of making a compound of Formula (I) is provided. The compound of Formula (I) may be prepared by a process comprising:

(a) providing a tryptamine compound having formula (2);

(b) adding a solution of the tryptamine compound (2), optionally in the presence of a base, to a withaferin-A compound (1) or a withanolide derivative thereof, such as compound (1-a);

(c) optionally heating the resulting reaction mixture; and (d) isolating the compound of Formula (I), or a salt thereof Scheme A

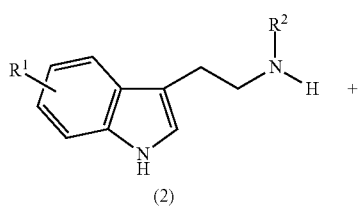

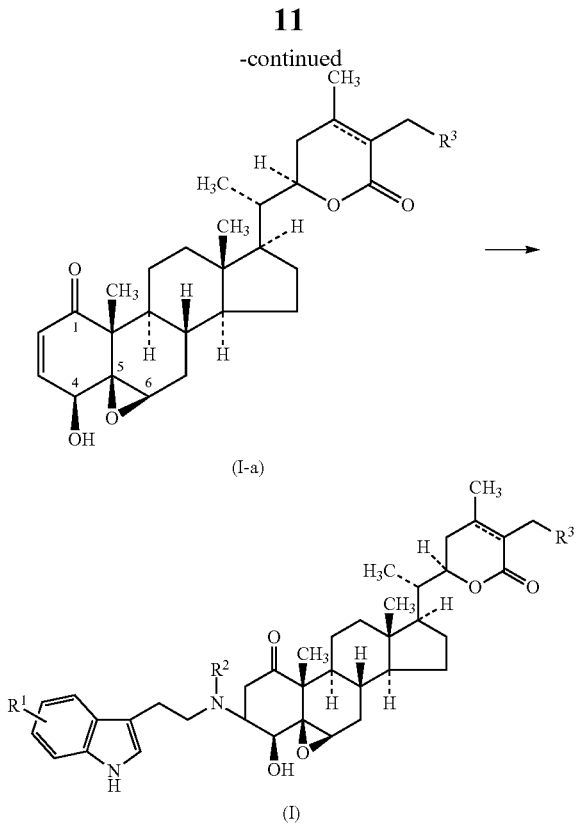

(I-a)

(I)

Optionally, the condensation reaction may be performed by adsorption on, or over, a solid support or catalyst. Useful solid support materials include alumina (neutral, acidic, or basic respectively), available from E. Merck, Darmstadt, Germany.

The synthesis is shown above in Scheme A, wherein $R^1$ is selected from the group consisting of hydrogen, $(C_1-C_3)$-alkyl hydroxyl, and $(C_1-C_4)$-alkoxy; wherein $R^2$ is hydrogen or $(C_1-C_3)$-alkyl; wherein $R^3$ is hydrogen or hydroxyl; and wherein ====== represents a single or a double bond. It is understood that the condensation reaction may provide one or more diastereomers having Formula (I), or mixtures thereof.

Without being bound by theory, it is believed that the presence of an α,β-unsaturated carbonyl moiety, with additional fortification by C4-OH and C5,6-epoxy groups in (1-a), or in general compound (B) of Scheme B, provides a synthetic route for its condensation under suitable conditions with corresponding nucleophiles (2), or general compound (A) of Scheme B by Michael 1,4 addition according to the following Scheme B.

Scheme B

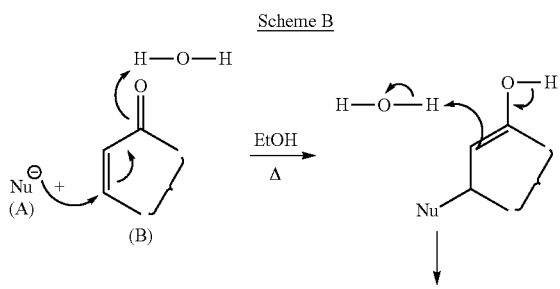

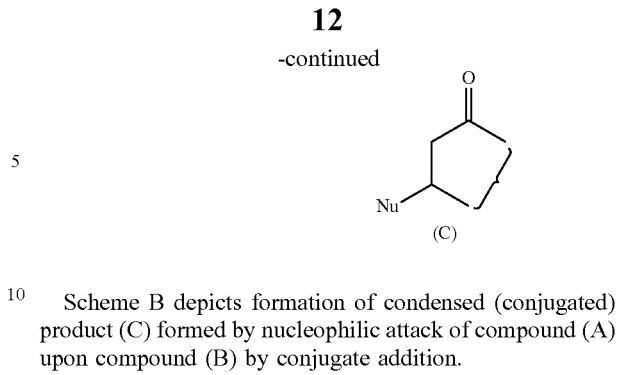

(C)

Scheme B depicts formation of condensed (conjugated) product (C) formed by nucleophilic attack of compound (A) upon compound (B) by conjugate addition.

Without being bound by theory, the chemical mechanism depicted in Scheme B is generally believed to represent a standard Michael 1,4 addition reaction. In a 1,4 Michael addition, a nucleophile (A) is condensed with a Michael acceptor, such as α,β-unsaturated ketone (B). Nucleophile (A) can include electron-rich chemical groups such as, for example, amines, alcohols, thiols, carbanions, and the like, or anions or salts thereof.

Thus, in accordance with Scheme B, compounds (1) or (1-a) reacted with a compound (2) would be expected to yield conjugate compounds having Formula (I) as shown.

Extraction of Indolealkylamino-withasteroid conjugates from *Withania somnifera*.

Dried roots and stalk (250 g, overground portions) of *Withania somnifera* were powdered and hot extracted on a steam bath at 80° C.±5° C. for 2 hours with purified water, filtered and evaporated to dryness under vacuum to give a solid WS aqueous extract (ca. 50 g). The solid WS aqueous extract was re-extracted with water (solid:solvent 1:10 (w/w)), on the steam bath at 80° C.±5° C. for 1 hour, and the extract collected. This re-extraction process was repeated twice more, and all three extracts were combined, and concentrated under vacuum to a combined liquid WS extract (ca. 50 ml). Acetone (ca. 450 ml) was then added dropwise until precipitation was complete. The mixture was kept overnight at room temperature (25° C.±5° C.), then filtered and the acetone soluble part (Acetone Soluble/WS Extract) was evaporated to dryness under reduced pressure by a rotary evaporator to afford a residue (19.25 g). The acetone insoluble precipitate was vacuum-dried and stored under vacuum (28.5 g).

A portion (2 g) of Acetone Soluble/WS Extract residue was then washed thoroughly with chloroform ($CHCl_3$), and the $CHCl_3$-insoluble solid (ca. 1 g) was re-dissolved in methanol (MeOH) and subjected to column chromatography on Silica gel (230-400 mesh). Elution started with 100% $CHCl_3$, followed by 5% increase in MeOH per column volume up to 25% MeOH. Two indolealkylamino-enriched fractions (IAEF-A, 120 mg, and IAEF-B, 90 mg) were obtained at 25% MeOH concentration. IAEF-A and IAEF-B were subjected to HPTLC analysis. UV reflectance spectrum and Ehrlich reagent was used for detection of indolealkylamino-withasteroid conjugates in the chromato-plates.

High performance thin-layer chromatography (HPTLC) analysis of IAEF-A and IAEF-B was performed on Merck KGaA 1.05554.0007 precoated TLC silica gel 60 $F_{254}$ Aluminium plates. IAEF-A and IAEF-B were dissolved in MeOH at a concentration of 1 mg/ml and applied on the TLC plates using CAMAG Linomet IV TLC applicator (available from CAMAG, Muttenz, Switzerland). The plates were developed in a twin trough chamber with $CHCl_3$: MeOH (95:5 v/v) as the mobile phase. Densitometric evaluation of the plates was performed at λ=225 nm, 366 nm and 560 nm (after derivatization by Ehrlich spray reagent), by means of a CAMAG TLC Scanner 3. The scanned data were processed by CAMAG winCATS software, version 1.3.4. The plates were subsequently scanned to determine the UV reflectance spectra of each spot, between 200 and 400 nm, and 400 to 800 nm (for Ehrlich-positive components) to identify the indolealkylamino-withasteroid conjugates.

IAEF-A was found to contain Ehrlich positive spots and the UV spectrum is consistent with indolealkylamino-withasteroid conjugates. IAEF-A was subjected to preparative thin layer chromatography (PTLC) after dissolving in MeOH, with a solvent system of $CHCl_3$:MeOH (95:5 v/v) to isolate the individual indolealkylamino-withasteroid conjugate fractions (IACs). (See Scheme 1 below for alternative column chromatographic separation.) Five different fractions were isolated and named as IAC1, IAC2, IAC3, IAC4 and IAC5. IAC2 was subjected to comprehensive chromatographic (HPTLC, HPLC, GC/MS) and spectroscopic (UV, NMR, MASS SPEC) analyses (see Example 1).

Figure 4A:
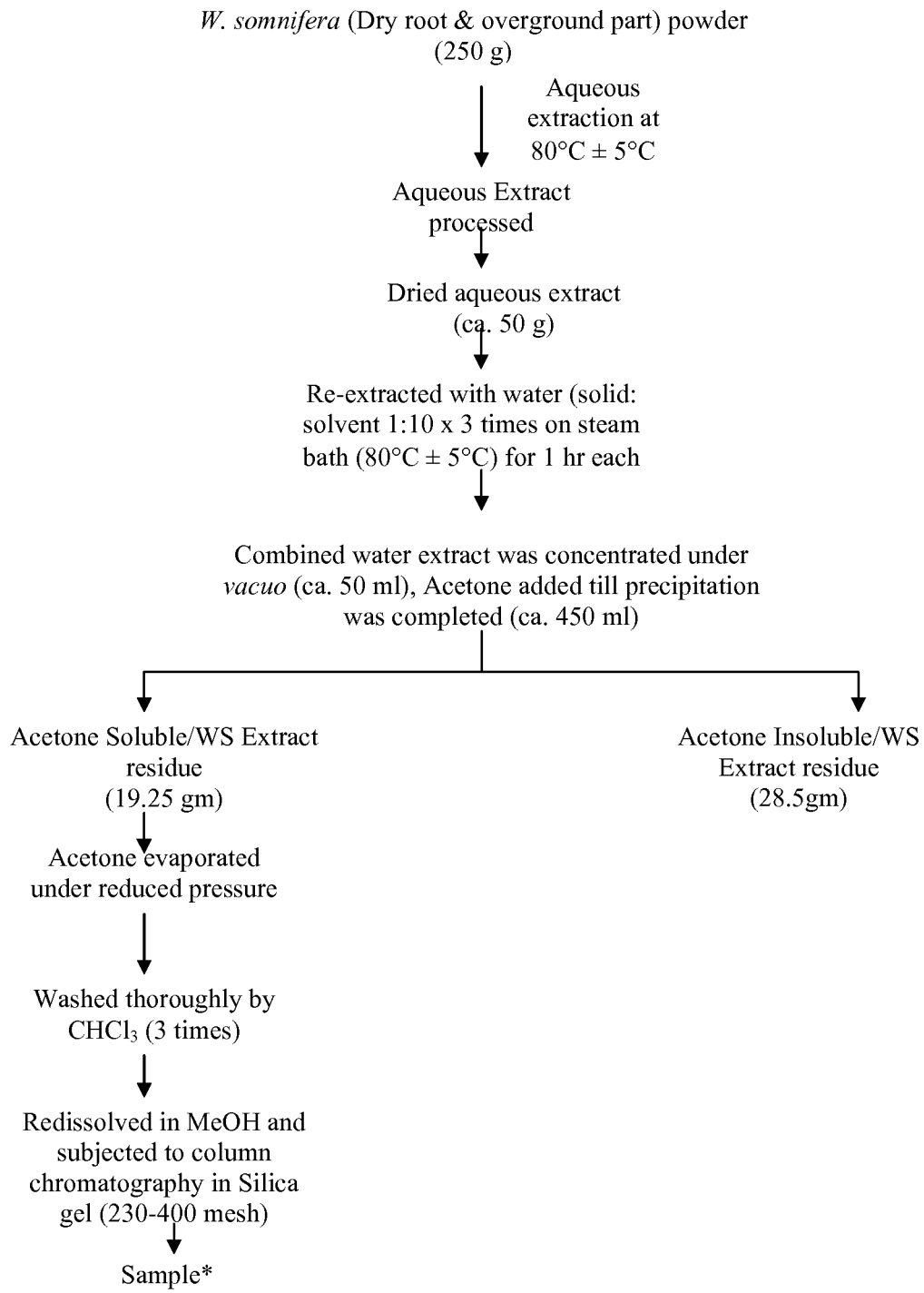
FIG. 4A is a flow diagram for extraction and processing of WS for isolation of indolealkylamino-withasteroid conjugates (IACs) as depicted by a flow diagram in Scheme 1.
Figure 4B:
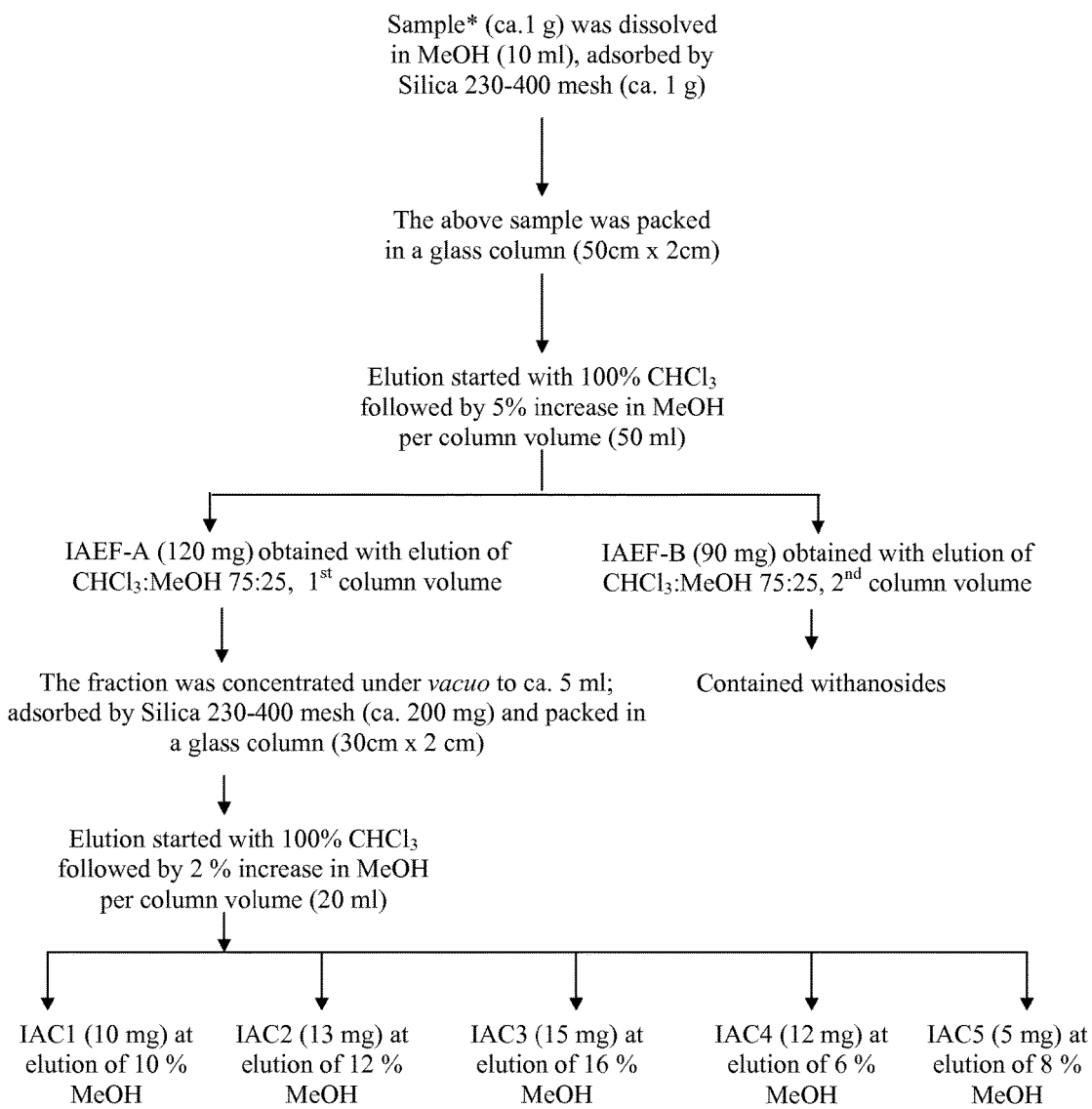
FIG. 4B is the flow diagram of FIG. 4A for extraction and processing of WS for isolation of indolealkylamino-withasteroid conjugates (IACs) as depicted by a flow diagram in Scheme 1, continued.

Details of the process are shown in Scheme 1 of FIGS. 4A and 4B, which is a flow diagram for extraction and processing of WS for isolation of indolealkylamino-withasteroid conjugates (IACs).

Optimization of the Extraction Process

The extraction process for WS can be optimized in accordance with the embodiments of the invention. In one aspect, the objectives of this study were to optimize the extraction procedure of fresh whole plant of Ashwagandha (*Withania somnifera*) in respect of (i) enrichment of the indolealkylamino-withasteroid conjugates (IACs), i.e., the compound of Formula (I) and derivatives thereof, and other withasteroids contents of the extractives, (ii) to meet the USP specification, and (iii) to assess the benefits of using water as the extraction solvent and modified conditions used in the extract preparation.

The results of an extraction process depend upon the solvent used, temperature of extraction and duration of the extraction process, among other parameters. In several embodiments of this invention, these parameters can be optimized to isolate and/or enrich and preserve the bioactive components of *Withania somnifera*.

Herbal extracts can be made by grinding the herbs into a fine powder and suspending the powder into a solution of alcohol and/or water. The solution is regularly agitated or pulverized (e.g., by ultrasonication) over time and then pressed through a filtering medium to extract the bio-active ingredients. Useful solvents for carrying out the extraction process can include water, alcohols such as methanol or ethanol, and the like. In one embodiment, it is desirable from an environmental point of view to have a method of extraction which is completely aqueous. This would also safeguard a recipient of the extract from ingesting methanol-solvated product.

In an embodiment, a process for making a *Withania somnifera* (WS) extract is provided. The invention further relates to a method for extracting *Withania somnifera* (WS) to obtain an powder enriched with withasteroids, and in particular, indolealkylamino-withasteroid conjugates (IACs), i.e., the compound of Formula (I) and derivatives thereof.

The extraction process includes the steps of: providing whole plant, over-ground portions, or root portions of *Withania somnifera* (WS); macerating the plant parts, or optionally, pulverizing or grinding the WS to a powder; extracting the WS material with an extraction solvent or solvent mixture, optionally, with heating, to provide a WS withanolide component enriched extract; and concentrating or drying the WS withanolide component enriched extract to provide WS withanolide component enriched extract powder. Aqueous solvent is preferred. A particularly preferred solvent is water. Useful extraction temperatures can range from about 50° C. to about 100° C., preferably from about 70° C. to about 100° C. A particularly useful extraction temperature is about 80±5° C. Useful extraction times in conjunction with the useful temperatures can range from about 1 hours to about 4 hours. A particularly useful extraction time range at about 80±° C. is from about 2 hours to about 4 hours, preferably about 3 hours.

Further extraction and purification steps are contemplated, including re-extraction into the same or different solvents, and chromatographic purification. The extracted products can also be further purified by crystallization, co-crystallization, precipitation, filtration, trituration using an appropriate solvent, or washing using an appropriate solvent, with or without mixing, agitation, or sonication. Combinations of the purification techniques are contemplated.

The extraction process can also include drying the extracted sample. Suitable drying methods include spray drying, lyophilization, vacuum drying and concentration under vacuum. Once isolated or obtained the WS withanolide component enriched extract powder may be processed by any suitable means, including grinding, milling, sieving, sizing, and the like. The obtained WS withanolide component enriched extract powder may be prepared in any suitable particle size, particle size range, or blend.

In the current extraction process, time and temperature are varied at atmospheric pressure (i.e., approx. 1 atm). It is contemplated that pressure can be varied in the extraction process, for example, by use of a pressure reactor apparatus that can provide pressures in excess of 1 atm.

Under the optimized conditions used, weight percent yields of IACs can range from about 0.2% by weight to about 2.5% by weight based on the total weight of WS extract. In a preferred embodiment, weight percent yields of IACs can range from about 0.2% by weight to about 1.6% by weight based on the total weight of WS extract. In another preferred embodiment, weight percent yields of IACs can range from about 0.75% by weight to about 1.6% by weight based on the total weight of WS extract.

Samples of Ashwagandh (*Withania somnifera*) plant were collected from medicinal plant garden, Rama Krishna Mission Ashrama (RKMA), Narendrapur, West Bengal.

HPLC Analytical Method for withanolides and withanosides adapted according to USP specification. IACs were also quantified using the same method, and isolated IAC 2 as an external marker.

The USP method is described herein.

Standard solution of Withanolide A: A quantity of USP Withanolide A was dissolved in methanol to obtain a solution having a known concentration of about 0.1 mg/ml.

Standard solution of Withanoside IV: A quantity of USP Withanoside IV was dissolved in methanol to obtain a solution having a known concentration of about 0.1 mg/ml.

Standard solution of USP Powdered WS Root Extract: 100 mg of USP Powdered *Ashwagandha* Extract Root was dissolved in 10 ml methanol, heated gently for approx. 15-20 min., diluted with methanol to volume. Before injection the solution was passed through a membrane filter of 0.45 μm and the filtrate was used for HPLC.

Standard solution of IAC: A quantity of IAC 2 (isolated and purified by Column chromatography; Scheme 1) was dissolved in methanol to obtain a solution having known concentration of 10 mg/ml.

WS extract solution: Samples extracted for specific time intervals were injected directly to HPLC and the concentrations were measured by the solvent content of the particular sample, e.g., as shown in Examples 4 and 5.

HPLC Conditions.

Column: reversed phase C18 LiChroCART, 250 mm 1.×4 mm i.d.

Column temp.: 27° C.

Flow rate: 1.5 ml/min.

Injection volume: 20 µl

Eluant: aqueous phase [A]: 0.14 g potassium dihydrogen phosphate in 1 liter water with 0.5 ml phosphoric acid; organic phase [B] acetonitrile (ACN).

Run Time: 40 min. Gradient: B 5-45% (18 min.), 45-80% (7 min.), hold 80% (3 min.), 80-5% (2 min.), hold 5% (10 min).

UV detection at 227 nm; Waters HPLC Model 515 with PDA detector (Waters™ 2996, Photodiode Array Detector), evaluation with Empower.

HPLC Evaluation Method. The method was developed with external standards as above and evaluation of area of peaks using the following equations.

Calculation of percentage of withanolides (or aglycones, "AG") in the samples.

$$\text{Percentage of Withanolides } (AG) = (r_{T1}/r_{S1})(C_{S1}/W) \times 1 \text{ g}/1000 \text{ mg} \times \text{sample vol. (ml)} \times 100$$

$r_{T1}$=sum of the peak responses for Withaferin A, Withanostramonolide, Withanolide A, Withanone and Withanolide B from sample solution.

$r_{S1}$=peak response of Withanolide A from USP standard Withanolide A solution.

$C_{S1}$=concentration of USP Withanolide A in Withanolide standard solution (mg/ml).

W=weight of powdered *Ashwagandha* extract taken to prepare the sample solution (g).

Calculation of percentage of withanosides (or withanolide glycosides, "WG") in the samples.

$$\text{Percentage of Withanosides } (WG) = (r_{T2}/r_{S2})(C_{S2}/W) \times 1 \text{ g}/1000 \text{ mg} \times \text{sample vol. (ml)} \times 100$$

$r_{T2}$=sum of the peak responses for Withanoside IV, V & VI from sample solution.

$r_{S2}$=peak response of Withanoside IV from USP standard Withanoside IV solution.

$C_{S2}$=concentration of USP Withanoside IV in Withanosides standard solution (mg/ml)

W=weight of powdered *Ashwagandha* extract taken to prepare the sample solution (g).

Calculation of percentage of IACs in the samples.

$$\text{Percentage of IACs} = (r_{T3}/r_{S3})(C_{S3}/W) \times \text{sample vol. (ml)} \times 100$$

$r_{T3}$=sum of the peak responses of peaks exhibiting $\lambda_{max}$ at 220, 280 & 320 nm.

$r_{S3}$=peak response of Standard Solution of IAC2

$C_{S3}$=concentration of IAC 2 in standard solution (g/ml).

W=Weight of *Ashwagandha* root extract taken to prepare the sample solution (g).

The present invention further embraces isolated compounds according to Formula (I). The expression "isolated compound" refers to a preparation of a compound of Formula (I), or a mixture of compounds according to Formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of Formula (I) or a mixture of compounds according to Formula (I), which contains the named compound or mixture of compounds according to Formula (I) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, preparative TLC, HPTLC, or HPLC. The preferred method for purification of the compounds according to Formula (I) or salts thereof comprises crystallizing the compound or salt from a solvent to form, preferably, a crystalline form of the compounds or salts thereof. Following crystallization, the crystallization solvent is removed by a process other than evaporation, for example filtration or decanting, and the crystals are then preferably washed using pure solvent (or a mixture of pure solvents). Preferred solvents for crystallization include water, alcohols, particularly alcohols containing up to four carbon atoms such as methanol, ethanol, isopropanol, and butal-1-ol, butan-2-ol, and 2-methyl-2-propanol, ethers, for example diethyl ether, diisopropyl ether, t-butyl methyl ether, 1,2-dimethoxyethane, tetrahydrofuran and 1,4-dioxane, carboxylic acids, for example formic acid and acetic acid, and hydrocarbon solvents, for example pentane, hexane, toluene, and mixtures thereof, particularly aqueous mixtures such as aqueous ethanol. Pure solvents, preferably at least analytical grade, and more preferably pharmaceutical grade are preferably used. In a preferred embodiment of the processes of the invention, the products are so isolated. In the compounds of the invention according to Formula (I) or salt thereof, and pharmaceutical compositions thereof, the compound according to Formula (I) or salt thereof is preferably in or prepared from a crystalline form, preferably prepared according to such a process.

The synthetic methods described above reflect a convergent synthesis strategy. Thus two components may be synthesized and elaborated separately prior to condensing or coupling the two compounds to form the target compounds. These convergent synthetic schemes allow for arrangement of the assembly steps of the backbone of the target compounds and derivatization of derivatizable functionalities to accommodate functional group sensitivity and/or to allow for functional groups or elements to be introduced either before or after the assembly of the backbone of the target compounds via the condensation or coupling reactions described.

It will be appreciated by one skilled in the art that certain aromatic substituents in compounds of the invention, intermediates used in the processes described above, or precursors thereto, may be introduced by employing aromatic substitution reactions to introduce or replace a substituent, or by using functional group transformations to modify an existing substituent, or a combination thereof. Such reactions may be effected either prior to or immediately following the processes mentioned above, and are included as part of the process aspect of the invention. The reagents and reaction conditions for such procedures are known in the art.

Specific examples of procedures which may be employed include, but are not limited to, electrophilic functionalization of an aromatic ring, for example via nitration, halogenation, or acylation; transformation of a nitro group to an amino group, for example via reduction, such as by catalytic hydrogenation; acylation, alkylation, or sulfonylation of an amino or hydroxyl group; replacement of an amino group by another functional group via conversion to an intermediate diazonium salt followed by nucleophilic or free radical substitution of the diazonium salt; or replacement of a halogen by another group, for example via nucleophilic or organometallically-catalyzed substitution reactions.

Additionally, in the aforesaid processes, certain functional groups which would be sensitive to the reaction conditions may be protected by protecting groups. A protecting group is a derivative of a chemical functional group which would otherwise be incompatible with the conditions required to perform a particular reaction which, after the reaction has been carried out, can be removed to re-generate the original functional group, which is thereby considered to have been "protected." Any chemical functionality that is a structural component of any of the reagents used to synthesize compounds of this invention may be optionally protected with a chemical protecting group if such a protecting group is useful in the synthesis of compounds of this invention. The person skilled in the art knows when protecting groups are indicated, how to select such groups, and processes that can be used for selectively introducing and selectively removing them, because methods of selecting and using protecting groups have been extensively documented in the chemical literature. Techniques for selecting, incorporating and removing chemical protecting groups may be found, for example, in *Protective Groups in Organic Synthesis* by Theodora W. Greene, Peter G. M. Wuts (John Wiley & Sons, Inc. 1999), the entire disclosure of which is incorporated herein by reference.

In addition to use of a protecting group, sensitive functional groups may be introduced as synthetic precursors to the functional group desired in the intermediate or final product. An example of this is an aromatic nitro ($-NO_2$) group. The aromatic nitro group does not undergo any of the nucleophilic reactions of an aromatic amino group. However, the nitro group can serves as the equivalent of a protected amino group because it is readily reduced to the amino group under mild conditions that are selective for the nitro group over most other functional groups.

It will be appreciated by one skilled in the art that the processes described are not the exclusive means by which compounds of the invention may be synthesized and that an extremely broad repertoire of synthetic organic reactions is available to be potentially employed in synthesizing compounds of the invention. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. Meth-Cohn, and C. W. Reese (Pergamon Press, 1996), *Comprehensive Organic Functional Group Transformations II*, Ed. A. R. Katritzky and R. J. K. Taylor (Editor) (Elsevier, $2^{nd}$ Edition, 2004), *Comprehensive Heterocyclic Chemistry*, Ed. A. R. Katritzky and C. W. Rees (Pergamon Press, 1984), *Comprehensive Heterocyclic Chemistry II*, Ed. A. R. Katritzky, C. W. Rees, and E. F. V. Scriven (Pergamon Press, 1996), and *Advanced Organic Chemistry*, $4^{th}$ Ed., J. March (John Wiley & Sons, 1992).

Salts of Compounds According to the Invention

The compounds of the present invention may take the form of salts. The term "salts" embraces addition salts of free acids or free bases which are compounds of the invention. The term "pharmaceutically-acceptable salt" refers to salts which possess toxicity profiles within a range that affords utility in pharmaceutical applications.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxyethanesulfonic, p-toluenesulfonic, sulfanilic, cyclohexylaminosufonic, stearic, alginic, β-hydroxybutyric, salicylic, galactaric and galacturonic acid. In the present examples of compounds of Formula (I), i.e., compounds containing amino groups, said compounds can be isolated as salts of inorganic acids or strong organic acids, e.g. hydrochloric acid or trifluoroacetic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine), tromethamine (tris(hydroxymethyl) aminomethane), and procaine.

All of these salts may be prepared by conventional means from the corresponding compound according to Formula (I) by reacting, for example, the appropriate acid or base with the compound according to Formula (I). Preferably the salts are in crystalline form, and preferably prepared by crystallization of the salt from a suitable solvent. The person skilled in the art will know how to prepare and select suitable salts forms for example, as described in *Handbook of Pharmaceutical Salts: Properties, Selection, and Use* by P. H. Stahl and C. G. Wermuth (Wiley-VCH 2002).

The nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. In accordance with one embodiment, suitable nutraceutically acceptable carriers can include ethanol, aqueous ethanol mixtures, water, fruit and/or vegetable juices, and combinations thereof Delivery System Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films or oral dissolvable strips can be used. Other useful delivery systems comprise oral or nasal sprays or inhalers, and the like.

For oral administration, a compound of Formula (I), or alternatively, a *Withania somnifera* (WS) extract may be further combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

The components of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof many comprise conventional ingredients in conventional proportions, with or without additional active compounds or principles, and such unit dosage forms may contain any suitable effective amount of the active ingredient commensurate with the intended daily dosage range to be employed.

The components of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired.

The powders and tablets preferably contain from five or ten to about seventy percent of the active compound(s). Suitable carriers are microcrystalline cellulose, sugar, lactose, pectin, dextrin, starch, gelatin, tragacanth, methylcellulose, sodium carboxymethlycellulose, a low melting wax, cocoa butter, and the like, and other excipients may include magnesium stearate, stearic acid, talc, silicon dioxide, etc. The term "preparation" is intended to include the formulation of the active compound with encapsulating material as carrier providing a capsule in which the active component, with or without carriers, is surrounded by a carrier, which is thus in association with it. Tablets, powders, capsules, pills, sachets, and lozenges are included. Tablets, powders, capsules, pills, sachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The chemical compound according to the present invention may thus be formulated for parenteral administration (e.g. by injection, for example bolus injection or continuous infusion) and may be presented in unit dose for in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Compositions suitable for topical administration in the mouth includes lozenges comprising the active agent in a flavored base, usually sucrose and *acacia* or tragacanth; pastilles comprising the active ingredient in an inert base such as gelatin and glycerine or sucrose and *acacia*; and mouthwashes comprising the active ingredient in suitable liquid carrier.

Solutions or suspensions are applied directly to the nasal cavity by conventional means, for example with a dropper, pipette or spray. The compositions may be provided in single or multi-dose form. In compositions intended for administration to the respiratory tract, including intranasal compositions, the compound will generally have a small particle size for example of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenges itself, or it can be the appropriate number of any of these in packaged form.

Tablets, capsules and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of Remington's Pharmaceutical Sciences (Mack Publishing Co., Easton, Pa.).

Solid nutritional compositions for oral administration may optionally contain, in addition to the above enumerated nutritional composition ingredients or compounds: carrier materials such as corn starch, gelatin, *acacia*, microcrystalline cellulose, kaolin, dicalcium phosphate, calcium carbonate, sodium chloride, alginic acid, and the like; disintegrators including, microcrystalline cellulose, alginic acid, and the like; binders including *acacia*, methylcellulose, sodium carboxymethylcellulose, polyvinylpyrrolidone, hydroxypropyl methylcellulose, ethyl cellulose, and the like; and lubricants such as magnesium stearate, stearic acid, silicone fluid, talc, waxes, oils, colloidal silica, and the like. The usefulness of such excipients is well known in the art.

Liquid nutritional compositions for oral administration in connection with a method for preventing and/or treating inflammation, colds and/or flu can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, *acacia*, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations (RTD's) are contemplated.

Routes of Administration

The compositions may be administered by any suitable route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflations, including powders and liquid aerosol administration, or by sustained release systems. Suitable examples of sustained release systems include semipermeable matrices of solid hydrophobic polymers containing the compound of the invention, which matrices may be in form of shaped artices, e.g. films or microcapsules.

The methods described above may be further understood in connection with the following Examples. In addition, the following non-limiting examples are provided to illustrate the invention. The results of an extraction process depend upon the solvent used, temperature of extraction and duration of the extraction process. In several embodiment of this invention, these factors can be optimized to isolate and/or enrich and preserve the bioactives of *Withania somnifera* (WS). WS as used in the following examples was obtained from Rama Krishna Mission Ashrama (RKMA), Narendrapur, Kolkata, West Bengal, India. GC-MS analysis was carried out on a Varian GC-MS, Model: Saturn 2000, GC 3800; equipped with a VF-5 MS 5% Phenyl-methyl polysiloxane column (30 m×0.25 mm i.d.). Carrier gas used was ultra pure Helium. All the analytical data of GC-MS analysis were based on Varian MS workstation software. 20 µl samples was taken in a glass vial and evaporated with $N_2$ gas and after that kept in vacuum for overnight. Then 40 µl Pyridine and 40 µl N,O-Bis(trimethylsilyl)acetamide reagent were added, mixed well and kept at 70° C. for 30 min for complete derivatization. Carrier gas used was ultrapure Helium with a constant flow rate of 1.2 ml/min. The GC oven temperature was programmed as follows: first step: initial temperature was 50° C. and hold time for 1 min; second step: final temperature was 100° C. with an increment of 10° C./min and hold time for 2 min; third step: final temperature was 125° C. with an increment of 10° C./min and hold time for 3 min; fourth step: final temperature was 150° C. with an increment of 10° C./min and hold time for 3 min; fifth step: final temperature was 180° C. with an increment of 10° C./min and hold time for 3 min; sixth step: final temperature was 200° C. with an increment of 20° C./min and hold time for 3 min; seventh step: final temperature was 280° C. with an increment of 20° C./min and hold time for 12 min. The samples were injected using split ratio of 1:20. The transfer line temperature was 260° C. and the injection volume was 0.5 µL. The conditions for mass spectrometer were as follows: mass range was 50-550, ionization potential: 70 eV, Emission current: 10 micro amps, ion trap temperature: 180° C., manifold temperature: 45° C. and background mass: 35 m/z.

Example 1

Synthetic Preparation of Indolealkylamino-Withasteroid Conjugate (IAC)

Example 1A

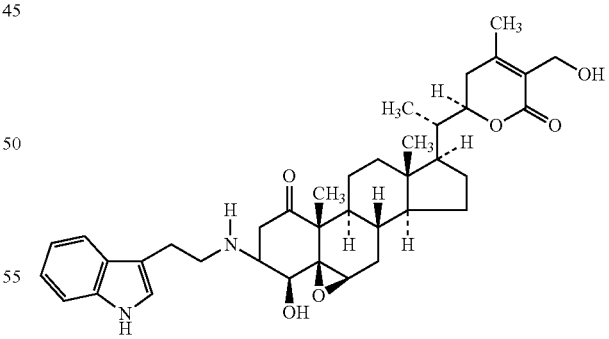

Indolealkylamino-withasteroid conjugate: Compound of Formula (I): $R^1$=hydrogen, $R^2$=hydrogen, $R^3$=hydroxyl, and ------ is a carbon-carbon double bond. Solution Phase. Tryptamine hydrochloride (3.6 mg) was taken in a 50 ml round bottom flask and dissolved in 200 µl distilled water. The solution was neutralized and basified by adding 200 µl ammonia. The excess ammonia was removed under a stream of nitrogen.

In a typical experiment, tryptamine (2.85 mg) thus prepared in the round bottom flask was dissolved in 20 ml aldehyde-free ethanol. Withaferin-A (9.4 mg) was added to the solution and the mixture was refluxed for 1 hr. After 1 hr, the mixture was allowed to cool and subjected to HPTLC and HPLC analyses for the identification of one or more conjugate(s).

Comparative HPTLC analyses of Tryptamine-Withaferin A Conjugates. HPTLC of Tryptamine-Withaferin A conjugates along with tryptamine-HCl and Withaferin A were performed on Merck KGaA; 1.05554.0007 precoated TLC aluminium sheets silica gel 60 $F_{254}$ plates. Samples were dissolved in ethanol at a concentration of 2 mg/ml and applied on the TLC plates using CAMAG Linomet IV TLC applicator. The plates were developed in a twin trough chamber with chloroform:methanol (90:10) as mobile phase. Densitometric evaluation of the plates was performed at $\lambda=254$ nm, 366 nm and 660 nm (after derivatization by Ehrlich spray reagent) by means of a CAMAG TLC Scanner 3. The scanned data were processed by CAMAG winCATS software, version 1.3.4. The plates were subsequently scanned to determine the UV reflectance spectra of each spot, between 200 and 400 nm, to identify the tryptamine-withaferin A conjugated compounds.

At 254 nm: HPTLC (elution $R_f$, relative abundance %): tryptamine (0.01, 24.40%); indolealkylamino-conjugate spot 1 (0.46, 6.53%); indolealkylamino-conjugate spot 2 (0.42, 4.09%); indolealkylamino-conjugate spot 3 (0.23, 24.14%); withaferin-A (0.65, 40.84%). UV $\lambda$max nm (Abs.): indolealkylamino-conjugate spot 1:234 (0.95), 297 (0.59); indolealkylamino-conjugate spot 2: 231 (0.95), 293 nm (0.64); indolealkylamino-conjugate spot 3: 234 (0.94), 295 nm (0.58).

Indolealkylamino-withasteroid conjugate: Compound of Formula (I): $R^1$=hydrogen, $R^2$=hydrogen, $R^3$=hydroxyl, and ------ is a carbon-carbon double bond. Preparation on a Solid Surface. The title compound was prepared by adsorption over alumina.

1A.1. Effect of Tryptamine and Withaferin-A Molar Ratios on the Yield of the Tryptamino-Withaferin-A Conjugate.

The effect of the molar ratio of reactants (tryptamine and withaferin-A) on the yield of tryptamino-withaferin-A conjugate was determined on a solid neutral alumina surface. The experiments were carried out with the different ratios (1:1.5, 1:2, 1:3) of tryptamine: withaferin-A. In a typical reaction, Tryptamine-HCl (16 mg) was weighed, taken in a conical flask and dissolved in 0.2 ml of Millipore deionized water. To the solution, 0.2 ml of ammonia solution was added and the mixture was warmed on steam bath until the smell of ammonia faded. Tryptamine thus formed was dissolved in 5 ml of ethanol. To the ethanolic solution of Tryptamine, 70.5 mg of Withaferin-A was added (to maintain 1:1.5 molar ratio of Tryptamine:Withaferin-A). The solution was taken on a petri dish and 1100 mg of alumina was added to the solution (to maintain 1:10 sample:alumina ratio) to adsorb Tryptamine-Withaferin-A mixture over alumina bed. The bed was kept at room temperature for 24 h without covering and shaking Another two sets of experiments were carried out as above using two different ratios of tryptamine and withaferin-A (tryptamine 16 mg:withaferin-A 94 mg; tryptamine 16 mg:withaferin-A 141 mg). After 24 h, the alumina bed containing the sample was taken in a conical flask and eluted by 50 ml (25 ml×2) of methanol with constant shaking for 5 minutes. The methanolic solution was filtered, evaporated under reduced pressure by rotary evaporator at 40° C. Tryptamine-withaferin-A conjugate thus formed under different ratios were subjected to comprehensive HPTLC analyses. The results are incorporated in Table A. Aluminum oxide was active, neutral Activity I-II, Merck Specialities Private Limited, Mumbai, India.

HPTLC Analyses of the Conjugates.

HPTLC analysis of the reaction products along with tryptamine-HCl, 5-methoxytryptamine and Withaferin-A were performed on Merck KGaA; 1.05554.0007 precoated TLC aluminium sheets silica gel 60 $F_{254}$ plates. Samples (1 mg each) were dissolved in 500 µl of ethanol at a concentration of 2 mg/ml and applied on the TLC plates using CAMAG Linomet IV TLC applicator. The plates were developed to 80 cm in a twin trough chamber with chloroform:methanol (95:5) as mobile phase. Densitometric evaluation of the plates was performed at $\lambda=254$ nm and 660 nm (after derivatization by Ehrlich spray reagent) using CAMAG TLC Scanner 3 in absorbance and fluorescence (for 366 nm) mode. The scanned data were processed by CAMAG winCATS software, version 1.3.4. The plates were subsequently scanned to determine the UV reflectance spectra of each spot, between 200 and 400 nm, to identify the indolealkylamino-withaferin-A conjugates.

TABLE A

Effect of tryptamine and withaferin-A molar ratios on the yield of the tryptamino-withaferin-A conjugate

| Tryptamine:Withaferin-A ratio | Unreacted Tryptamine (% w/w) | Unreacted Withaferin-A (% w/w) | Tryptamino-withaferin-A conjugate (% w/w) |
|---|---|---|---|
| 1:1.5 | 36.75 | 10 | 53 |
| 1:2 | 24.5 | 13 | 62 |
| 1:3 | 19.5 | 36.7 | 43 |

The results from the above study indicates that tryptamine:withaferin-A 1:2 molar ratio was found as the optimum ratio for the synthesis of tryptamino-withaferin-A conjugate. Therefore, further experiments were carried out using the 1:2 tryptamine:withaferin-A ratio, as follows.

1A.2. Effect of pH of the Solid Surface (Alumina) on the Yield of the Tryptamino-Withaferin-A Conjugate.

The effect of pH of the solid surface (alumina) on the yield of tryptamino-withaferin-A conjugate was studied using acidic alumina (Aluminum oxide active, acidic Activity I-II, Loba Chemie Private Limited, Mumbai, India pH 3.5-5.0), neutral alumina (Aluminum oxide active, neutral Activity I-II, pH 6.8-7.8, Merck Specialities Private Limited, Mumbai, India) and basic alumina (Aluminum oxide active, basic Activity I-II, Loba Chemie Private Limited, Mumbai, India pH 8.5-10). In a typical reaction, Tryptamine-HCl (16 mg) was weighed, taken in a conical flask and dissolved in 0.2 ml of millipore water. To the solution, 0.2 ml of ammonia solution was added and the mixture was warmed on steam bath until the smell of ammonia faded.

Tryptamine thus formed was dissolved in 5 ml of ethanol. To the ethanolic solution of Tryptamine, 94 mg of Withaferin-A was added (to maintain 1:2 molar ratio of Tryptamine:Withaferin-A). The solution was taken on a petri dish and 1100 mg of alumina was added to the solution (to maintain 1:10 sample:alumina ratio) to adsorb Tryptamine-Withaferin-A mixture over alumina bed. The bed was kept at room temperature for 24 h without covering and shaking Three different experiments were thus performed in the same manner using acidic, basic and neutral alumina to evaluate the optimum pH of the adsorption media for the conjugation reaction. After 24 h, the alumina bed containing the sample was taken in a conical flask and eluted by 50 ml (25 ml×2) of methanol with constant shaking for 5 minutes. The methanolic solution was filtered, evaporated under reduced pressure by rotary evaporator at 40° C. Tryptamine-withaferin-A conjugate thus formed under different pH conditions of the adsorbant (alumina) were subjected to comprehensive HPTLC analyses. The results are incorporated in Table B.

TABLE B

Effect of pH of the solid surface (Alumina) on the yield of the tryptamino-withaferin-A conjugate.

| pH of Alumina | Unreacted Tryptamine (% w/w) | Unreacted Withaferin-A (% w/w) | Tryptamino-withaferin-A conjugate (% w/w) |
|---|---|---|---|
| Neutral (pH 6.8-7.8) | 25 | 13 | 62 |
| Acidic (pH 3.5-5.0) | 42 | 46 | 12 |
| Basic (pH 8.5-10) | 25 | 32 | 43 |

The results shown above (Table B) indicate that neutral Alumina solid surface provided a better yield of tryptamino-withaferin-A conjugate (62%) than the acidic and basic alumina surfaces. Therefore, further experiments of conjugation were done using neutral alumina.

1A.3. Effect of the Ratio of Reactants and Solid Surface (Neutral Alumina) on the Yield of the Tryptamino-Withaferin-A Conjugate.

In another set of experiments, the effect of the ratio of the combined reactants (tryptamine and withaferin-A, 1:2) and solid surface component (neutral alumina) on the yield of tryptamino-withaferin-A conjugate was determined. The experiments were carried out as described above in the Example 1A.1 with the different ratios (1:2, 1:10, 1:20) of reactants and solid surface (neutral alumina), that is: reactants 110 mg:neutral alumina 220 mg, reactants 110 mg:neutral alumina 1100 mg, and reactants 110 mg:neutral alumina 2200 mg, respectively. The resultant products were analyzed by HPTLC (as described above) and the results are incorporated in Table C.

TABLE C

Effect of the ratio of reactants and solid surface (neutral Alumina) on the yield of the tryptamino-withaferin-A conjugate.

| Reactants:neutral Alumina ratio | Unreacted Tryptamine (% w/w) | Unreacted Withaferin-A (% w/w) | Tryptamino-withaferin-A conjugate (% w/w) |
|---|---|---|---|
| 1:2 | 47 | 33 | 20 |
| 1:10 | 25 | 13 | 62 |
| 1:20 | 24 | 12 | 64 |

The results shown above (Table C) using different ratios of the combined reactants:alumina indicated that 1:10 (reactants:alumina) provided much better yield (62%) of tryptamino-withaferin-A conjugate than 1:2 ratio.

Taken together, the above exemplary optimization experiments (1A.1 to 1A.3) suggest that the suitable and/or optimum conditions of tryptamino-withaferin-A conjugate synthesis are as follows:

Optimum molar ratio of tryptamine:withaferin-A is about 1:2.

Optimum pH of the solid adsorbent surface is neutral alumina (pH about 6.8-7.8).

Optimum ratio of combined reactants:solid adsorbent (neutral alumina) is about 1:10.

The conjugate thus prepared using optimized conditions was further purified by following graded solvent precipitation method. In a typical experiment, the crude product (ca. 100 mg) was dissolved in acetone (5 ml) and to that 40 ml of ethyl acetate was added slowly with continuous stirring. The solution was kept at 4° C. for 2 hrs for complete precipitation of un-reacted tryptamine. The solution was centrifuged at 8000 RPM for 5 minutes and the supernatant was evaporated to dryness under reduced pressure. The dry residue was re-dissolved in chloroform (5 ml), 40 ml of n-hexane was added to it and the mixture kept at 4° C., for 2 hrs, for complete precipitation of the tryptamino-withaferin-A conjugate (45 mg). The purified conjugate was subjected to comprehensive chromatographic (HPLC, HPTLC) and spectroscopic (UV, $^1$H-NMR, IR, Mass) analyses for structural characterization.

Tryptamino-withaferin-A conjugate (I): The molecular formula $C_{38}H_{40}O_6N_2$ was confirmed from the ESI-Mass analysis. The ESI-Mass analysis showed a positive ion at m/z 631.4 $(M+H)^+$. The UV spectrum in methanol showed absorption maxima at λmax 234 nm (0.95 AU) and 297 nm (0.59 AU); thus corresponding to above indolealkylamino-conjugate spot 1 of solution phase experiment. The 400 MHz $^1$H NMR (in $CD_3OD$) showed the presence of indole moiety protons δ 7.0-7.2 ppm (m, indolic H-4,6,7) and withaferin-A δ 0.9-1.98 (4×$CH_3$-groups).

Rationale for the point of conjugation of tryptamine (N) and withaferin-A ($C_3$-position): alkenyl protons (withaferin-A $C_2$, $C_3$—H) signals shifted upfield to methylene/methine regions from those in withaferin-A [δ 6.2 (d, steroidal C-2 proton) and δ 7.0 (m, steroid C-3 proton)]. These data demonstrated the point of attachment of indole-alkylamino moiety at the $C_3$-position of the withaferin-A moiety. FTIR (in KBR) revealed peaks v max at 3415 $cm^{-1}$ (hydroxyl group and α-β-unsaturated lactone), 2938 $cm^{-1}$ (alkyl CH) and 1689 $cm^{-1}$ (conjugated carbonyl function).

Example 2

Synthetic Preparation or Extraction of 5-Substituted Indolealkylamino-Withasteroid Conjugate (IAC)

Example 2A

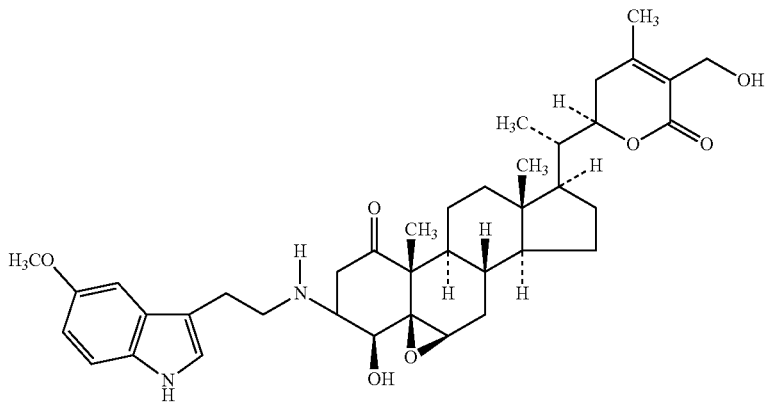

Indolealkylamino-withasteroid conjugate 2 (IAC2): Compound of Formula (I): $R^1$=5-methoxy, $R^2$=hydrogen, $R^3$=hydroxyl, and ===== is a carbon-carbon double bond. Preparation on a Solid Surface. The title compound was prepared by adsorption over neutral alumina. 5-methoxytryptamino-withaferin-A conjugate was prepared using the developed optimized conditions of the tryptamino-withaferin-A conjugate synthesis (as in Example 1A.3). In a typical experiment, 5-methoxytryptamine (18 mg) was weighed and dissolved in 5 ml of ethanol. To the ethanolic solution of 5-methoxytryptamine, 94 mg of withaferin-A was added (to maintain 1:2 molar ratio of 5-methoxytryptamine:withaferin-A). The solution was taken on a petri dish and 1100 mg of neutral alumina was added to the solution (to maintain 1:10 sample:alumina ratio) to adsorb 5-methoxytryptamino-withaferin-A over alumina bed. The bed was kept at room temperature for 24 h without covering and shaking After 24 h, the alumina bed containing sample was taken on a conical flask and extracted by 50 ml (25 ml×2 times) of methanol with constant shaking for 5 minutes each time. The methanolic solution was filtered, evaporated under reduced pressure by a rotary evaporator at 40° C. 5-methoxytryptamino—withaferin-A conjugate thus formed was further purified by graded solvent precipitation method as follows.

The above reaction product (ca. 100 mg) was dissolved in acetone (5 ml) and to that 40 ml of ethyl acetate was added slowly with continuous stirring. The solution was kept at 4° C. for 2 hrs for complete precipitation of un-reacted 5-methoxytryptamine. The solution was centrifuged at 8000 RPM for 5 minutes and the supernatant was evaporated to dryness under reduced pressure. The dry residue was re-dissolved in chloroform (5 ml), 40 ml of n-hexane was added to it and kept at 4° C., for 2 hrs, for complete precipitation of the 5-methoxytryptamino-withaferin-A conjugate (45 mg). The purified conjugate was subjected to comprehensive chromatographic (HPLC, HPTLC) and spectroscopic (UV, $^1$H-NMR, IR, Mass) analyses for structural characterization.

5-Methoxytryptamino-withaferin-A conjugate (I): The molecular formula $C_{39}H_{52}O_7N_2$ was confirmed from the ESI-Mass analysis. The ESI-Mass analysis showed a positive ion at m/z 661.4 $(M+H)^+$. The UV spectrum in methanol showed absorption maxima at λmax 236 nm (0.95 Au) and 299 nm (0.70 Au). The $^1$H NMR (in $CD_3OD$) showed the presence of indole moiety: multiplet protons, centered at δ 7 ppm (6.7-7.3 ppm). The ($C_2,C_3$—H) protons of withaferin-A were shifted upfield in the 5-methoxytryptamino-withaferin-A conjugate thereby supporting the point of attachment of the conjugate as shown. FTIR (in KBR) revealed peaks at 3407 $cm^{-1}$ (hydroxyl group and α,β-unsaturated lactone), 2935 cm-1 (alkyl CH) and 1684 cm-1 (conjugated carbonyl function).

In vitro pharmacology results for Examples 2A and 1A, and also in vivo testing results, are described in Example 7 below.

Example 2B

Indolealkylamino-withasteroid conjugate 2 (IAC2): Compound of Formula (I): $R^1$=5-methoxy, $R^2$=hydrogen, $R^3$=hydroxyl, and ===== is a carbon-carbon double bond. Extraction enriched in indolealkylamino-withasteroid conjugates having Formula (I). The general extraction and isolation procedure of Scheme 1 was carried out as discussed above. Based on an indolealkylamino-withasteroid enriched fraction IAEF-A (120 mg), IAC2 was isolated by column chromatography (13 mg). UV $\lambda_{max}$ (MeOH): nm (Abs.) 212 (0.52), 235 sh (–), 295 (0.033). MS (EI) The molecule fragmented before exhibiting an $M^{+\bullet}$ peak; the fragment ion peaks appeared at m/z 648, 645 (M-15), 633, 615, 169, 160, 145, 123. GC/MS intense signal at $t_R$ 16.156 min; fragment ions:withaferin moiety m/z 328, 286, 193, 175, 147, 141, 117, indolealkylamino-moiety, after autooxidation m/z 207, 190, 189, 162, 161. $^1$H-NMR (300 MHz, $CD_3OD$) δ 0.9-1.98 (4×$CH_3$-groups), 6.5-7 (indolic H-4,6,7); interpretation: alkenyl protons absent, signals shifted upfield to methylene/methane regions relative to withaferin A δ 6.3 (steroidal C-2 proton, d) and 7.0 (steroid C-3 proton, q), demonstrating point of attachment of indolealkylamino-moiety.

Example 3

In Vitro Inhibition of Acetylcholine-Esterase Activity

The WS dried aqueous extract (WS-74), acetone soluble/WS extract fraction (Ace Sol/WS-74), indolealkylamino-withasteroid conjugate enriched fraction (IAEF-A), the isolated pure compounds (IAC 1-5), and withaferin A, among other comparative samples, were subjected to in vitro acetylcholinesterse activity assay to determine their anti-cholinesterase activity (see also Scheme 1 above). The acetylcholinesterase (AChE) assay was performed by the method of Ellman et al., with minor modification, using acetylthiocholine Iodide as a substrate (G. L. Ellman, et al., "A new and rapid colorimetric determination of acetylcholinesterase activity," *Biochem. Pharmacol.* (1961) 7: 88-95). Ellman's reaction mixture was made from a combination of 10 mM Acetylthiocholine iodide and 0.5 mM 5,5'-dithio-bis-(2-nitrobenzoic acid) in a 0.05 M sodium phosphate buffer (pH 7.2). The rates of hydrolysis by AChE were monitored spectrophotometrically using a 96-well microtiter plate reader. Each test sample (10 µl) and 0.05 M sodium phosphate buffer (30 µl) was mixed with the enzyme solution (10 µl). An Ellman's reaction mixture (50 µl) was further added to give a final volume of 100 µl, and the mixture was incubated at 37° C. for 30 min. Absorbance at 450 nm was recorded immediately after adding the Ellman's reaction mixture. Reading was repeated for 10 min at 2 min intervals to verify that the reaction occurred linearly. Blank reaction was measured by substituting saline for the enzyme (Y. K. Chung, et al., "Inhibitory effect of ursolic acid purified from *Origanum majorana* L. on the acetylcholinesterase," Mol. Cells (2001) 11: 137-143).

Figure 1B:
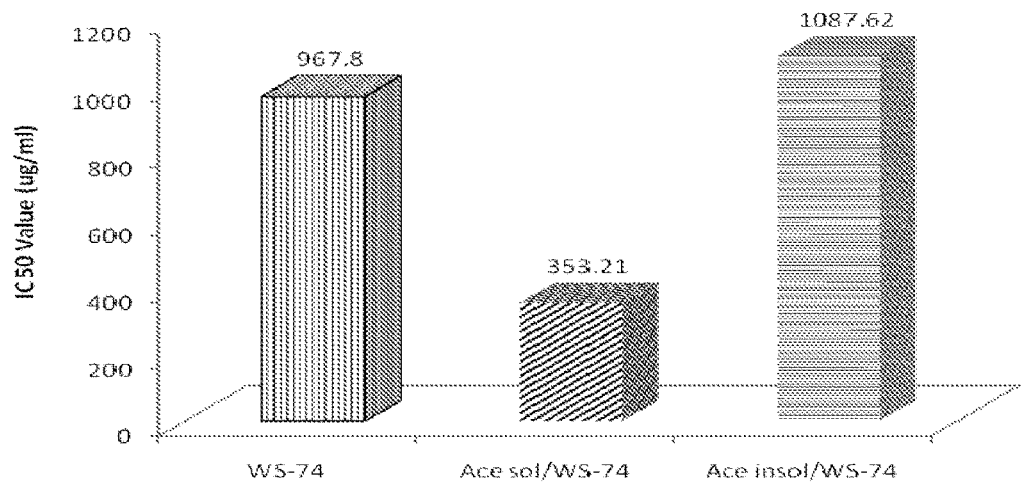
FIG. 1B is a bar graph depicting $IC_{50}$ values for acetylcholinesterase inhibition by the WS extract test samples of FIG. 1A.

The WS dried aqueous extract (WS-74), acetone soluble/WS extract fraction (Ace Sol/WS-74), and acetone insoluble/WS extract fraction (Ace insol/WS-74) were tested as described above to afford acetylcholinesterase inhibition data and $IC_{50}$'s. The results as depicted in FIGS. 1A and 1B showed that WS-74, Ace Sol/WS-74 and Ace Insol/WS-74 exhibited good dose-dependent in-vitro acetylcholinesterase inhibitory activity. However, the activity of Ace Sol/WS-74 was found to be more potent than the other two samples, as indicated by the top line observed in FIG. 1A. Withaferin-A exhibited only feeble inhibitory activity (not shown).

In FIGS. 1A and 1B it was evident that Ace Sol/WS-74 is a more potent in vitro acetylcholinesterase inhibitor in comparison with the other samples. Thus, this fraction was further purified into two fractions by column chromatography, namely, two indolealkylamino-enriched fractions (IAEF-A and IAEF-B). These two samples were also assessed for in vitro acetylcholinesterase inhibitory activity. The inhibition percentages and $IC_{50}$'s of the test samples were incorporated in FIGS. 2A and 2B, respectively.

Figure 2A:
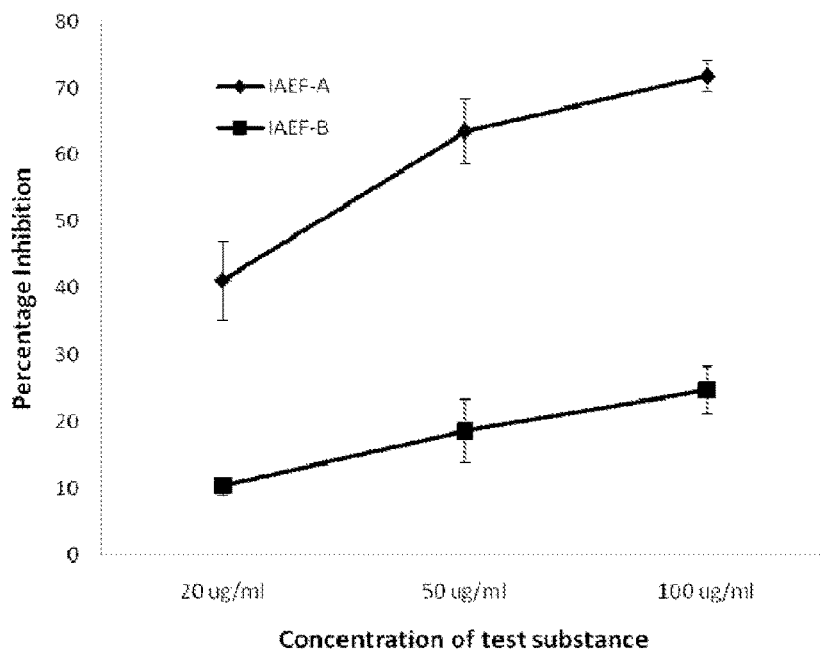
FIG. 2A depicts percent inhibition of acetylcholinesterase by two indolealkylamino-enriched fractions (IAEF-A and IAEF-B) of a WS extract as a function of concentration.
Figure 2B:
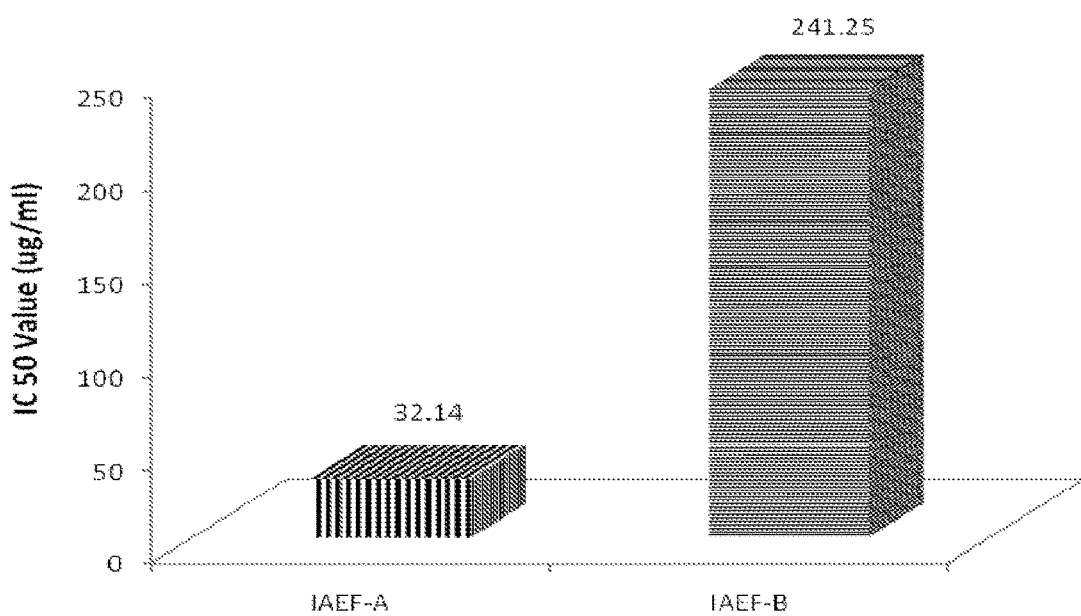
FIG. 2B is a bar graph depicting $IC_{50}$ values for acetylcholinesterase inhibition by the WS extract test samples of FIG. 2A.
Figure 3A:
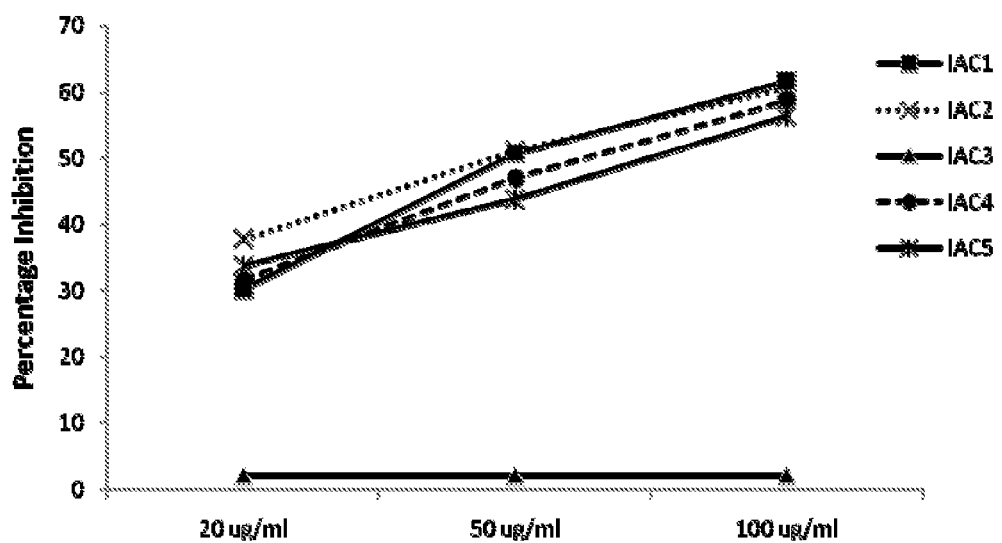
FIG. 3A depicts percent inhibition of acetylcholinesterase by five indolealkylamino-withasteroid conjugate compounds (IAC's 1-5) derived from indolealkylamino-enriched fraction (IAEF-A) as a function of concentration.
Figure 3B:
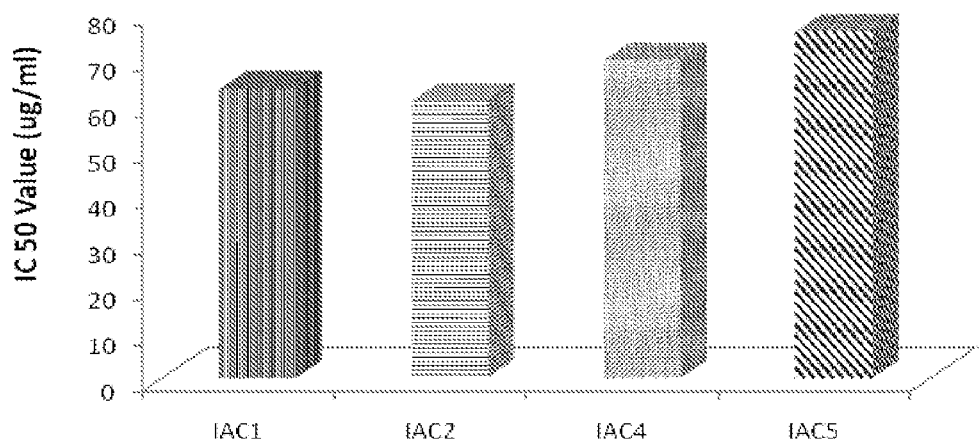
FIG. 3B is a bar graph depicting $IC_{50}$ values for acetylcholinesterase inhibition by the IAC 1, 2, 4 and 5 test samples of FIG. 3A.

In FIGS. 2A and 2B it was evident that, IAEF-A is a superior in vitro acetylcholinesterase inhibitor over IAEF-B. Thus, IAEF-A was further fractioned into five indolealkylamino-withasteroid conjugate compounds: IAC1, IAC2, IAC3, IAC4 and IAC5 by column chromatography and preparative TLC, as described above. These five compounds were also tested for in vitro acetylcholinesterase inhibitory activity. The results are depicted in FIGS. 3A and 3B.

Among the five test samples, only IAC3 did not show any in vitro acetylcholinesterase inhibitory activity. All of the remaining indolealkylamino-withasteroid conjugate test samples showed comparable activities in this assay system. The $IC_{50}$ values of these isolated individual compounds ranged from 60-80 µg/ml, and thus were observed to be slightly less potent than the mother fraction (IAEF-A, $IC_{50}$ value 32.14 µg/ml), which indicates synergistic activity among one or more of these indolealkylamino-withasteroid conjugates (IACs).

Example 4

Effect of *Withania somnifera* (WS) extract and its fractions on Scopalamine-induced amnesia and anxiety paradigms in vivo.

Experimental animals. Swiss Albino mice of both sexes weighing approximately 32±4 g, 10-15 weeks old were obtained from National Research Institute of *Ayurveda* for Drug Development (Govt. of India), Kolkata, and were housed in polypropylene cages at 22±3° C. and relative air humidity of 45-55%, with 12.00 hour light & dark cycle (lighting on from 6:00 AM to 6:00 PM). Mice were provided a standard pellet chow (carbohydrate 65.5%, protein 17.6%, fat 6.6%) and distilled water ad libitum. The mice were acclimatized for one week in the laboratory conditions, before being used in the experiment. All experiments were conducted between 10:00 AM and 2:00 PM. Principles of laboratory animal care (NIH publication no. 85-23, revised 1885) were always followed.

Drug preparation and administration of doses. Test samples were suspended in 0.3% Carboxymethyl Cellulose (CMC) solutions of distilled water and were administered orally for 16 days by using an intubation canula, and volume of dose was 0.1 ml/10 g body weight. WS dried aqueous extract (WS-74), its fractions, acetone soluble/WS extract fraction (Ace Sol/WS-74) acetone insoluble/WS extract (Ace Insol/WS-74), and indolealkylamino-withasteroid conjugate enriched fraction (IAEF-A), and Withaferin-A (1) were administered orally for 16 days in 0.3% CMC solution. The experiments were carried out after 45 minutes of the administration of the drugs. Control animals received equivalent volume of the vehicle, 0.3% CMC solution, only.

Example 4A

Scopolamine-Induced Amnesia

Alzheimer's disease is associated with significant losses in cholinergic neurons and decreased concentrations of the neurotransmitter, acetylcholine, which is significantly involved in learning and memory processes. Scopolamine hydrobromide produces amnesia in mice because of its anti-cholinergic action. Scopolamine hydrobromide exerts its effects by acting as a competitive antagonist at muscarinic acetylcholine receptors, specifically M1 receptors. Because of its anti-cholinergic effects, scopolamine hydrobromide has been shown to prevent the activation of medial temporal lobe structures for novel stimuli during spatial memory tasks. It has also been shown to impair memory in humans in a manner mimicking the cognitive deficits found in Alzheimer's Dementia. Therefore, in the present study, a scopolamine hydrobromide-induced amnesic model using elevated plus maze was selected to evaluate the anti-amnesic effects of WS extract and its fractions (as prepared above). The elevated plus maze is used to measure the memory learning activity in mice; however, transfer latency, i.e., the time elapsed between the movement of the animal from an open to an enclosed arm was markedly shortened if the animal had previously experienced entering open and closed arms.

Amnesia was induced by administration of scopolamine hydrobromide (0.5 mg/kg, i.p.) on the $8^{th}$ day immediately after the learning trial. Retention was recorded after 24 hrs ($9^{th}$ day) and after an interval of one week ($16^{th}$ day).

Drug protocol. The animals were divided into 7 groups (Group I-VII) of eight animals in each group. Group I received vehicle (0.3% CMC only) and served as vehicle control. Groups II-VII were treated with the respective test drugs, as per the details mentioned in Table 1 below, for 16 days. Scopolamine hydrobromide (0.5 mg/kg, i.p.) was administered to groups II-VII on the 8th day immediately after the learning trial. Transfer Latency was recorded after 45 minutes of the drug administration on 8th day (learning trial) and 24 hrs (9th day) and one week (16th day) after learning trial.

TABLE 1

| Groups | Treatment | Doses mg/kg, b.w.; route of administration |
|---|---|---|
| I | Vehicle (0.3% CMC) | 0.1 ml/10 g, b.w.; p.o. |
| II | SH | 0.5; i.p. |
| III | WS extract (WS-74) + SH | 50; p.o. + 0.5; i.p. |
| IV | Ace Sol/WS-74 + SH | 20; p.o.+ 0.5; i.p. |
| V | Ace Insol/WS-74 + SH | 30; p.o. + 0.5; i.p. |
| VI | IAEF-A + SH | 1; p.o. + 0.5; i.p. |
| VII | Withaferin-A (1) | 1; p.o. + 0.5; i.p. | n = 8 animals in each group,
b.w. = body weight,
SH = Scopolamine Hydrobromide,
p.o. = oral administration,
i.p. = intraperitoneal administration.

The doses of different fractions as listed in Table 1, namely, Ace Sol/WS-74, Ace Insol/WS-74, IAEF-A, Withaferin-A, were calculated based on their abundance percentage in the WS extract (WS-74). See also Scheme 1.

Retention in elevated plus maze test was used to assess the memory functions in test animals. The plus maze consists of two open opposite arms, (50×10 cm) length×width, crossed with two enclosed arms of same dimensions with walls 40 cm high. The arms are connected with a central square, (10×10 cm) to give the apparatus a plus-sign appearance. The maze was kept elevated 50 cm above the floor in a dimly lit room. On day 8, mice were individually placed on far end of one of the open arms facing away from the center and transfer latency (TL) on day 8 was recorded. TL is the time taken by the mouse to move into any one of the covered arms with all its four legs. The mice were left in the enclosed arms for 10-15 s and then were taken to the home cage. On day 9, the mice were again placed on the far end of the open arm and time taken by the mice to enter the enclosed arm, transfer latency (TL) day 9, was recorded. Similarly after an interval of one week, on day 16, the transfer latency (TL) day 16 was again recorded. (J. Itoh, et al., "Utility of an elevated plus maze for the evaluation of nootropics, scopolamine and electro convulsive shock," *Psychopharmacol.* (1990): 101:27-33; M. Parle, et al., "Improvement of mouse memory by *Myristica fragrans* seeds," *J Med. Food.* (2004) 7:157-61; and H. Joshi, et al., "Brahmirasayana Improves Learning and Memory in Mice," *eCAM* (2006) 3: 79-85.)

The retention scores were obtained for each animal by calculating percent decrease in latency period by the formula:

% decrease in $TL = (L_1 - L_0/L_0) \times 100$ where, $L_0$=initial transfer latency period in seconds, and $L_1$=transfer latency after 24 hrs, or one week.

Results of the Scopolamine-induced amnesia experiment are presented in Tables 2-5 following.

TABLE 2

Effect of different treatments on Transfer Latency of Scopolamine-induced amnesic mice on elevated plus maze

| Treatment | Transfer Latency (s) | | |
|---|---|---|---|
| Group[1] (mg/kg) | Day 8 | Day 9 | Day 16 |
| Vehicle (0.3% CMC) | 184.50 ± 30.73 | 86.50 ± 14.11 | 75.88 ± 12.30 |
| SH (0.5) | 171.50 ± 16.08 | 143.90 ± 15.30* | 133.10 ± 15.95** |
| WS extract (WS-74) (50) + SH (0.5) | 147.40 ± 14.93 | 61.63 ± 7.05$$$ | 53.00 ± 6.00$$$ |
| Ace Sol/WS-74 (20) + SH (0.5) | 128.80 ± 11.00 | 55.13 ± 15.27$$$ | 47.50 ± 5.21$$$ |
| Ace Insol/WS-74 (30) + SH (0.5) | 212.00 ± 4.25 | 136.60 ± 15.92 | 120.60 ± 16.56 |
| IAEF-A (1.0) + SH (0.5) | 108.40 ± 10.16 | 34.88 ± 6.76$$$ | 27.38 ± 5.68$$$ |
| Withaferin-A (1) + SH (0.5) | 180.40 ± 8.04 | 124.00 ± 13.27 | 114.90 ± 13.10 |

[1]As in Table 1; SH = Scopolamine Hydrobromide
Values were expressed in mean ± SEM (n = 8). P values were obtained by ANOVA followed by post hoc comparison between groups by Newman-Keuls test.
*p < 0.05;
**p < 0.01;
***p < 0.001; in comparison to vehicle treatment after 24 hrs.
$p < 0.05;
$$p < 0.01;
$$$p < 0.001; in comparison to SH treatment after one week.

TABLE 3

Effect of different treatments on Transfer Latency of Scopolamine-induced amnesic mice on elevated plus maze (After 24 h; i.e., on day 9)

| Treatment Group (mg/kg) | % Decrease in Transfer Latency, Mean ± SEM |
|---|---|
| Vehicle (0.3% CMC) | 51.13 ± 4.97 |
| SH (0.5) | 14.91 ± 5.75 |

TABLE 3-continued

Effect of different treatments on Transfer Latency of Scopolamine-induced amnesic mice on elevated plus maze (After 24 h; i.e., on day 9)

| Treatment Group (mg/kg) | % Decrease in Transfer Latency, Mean ± SEM |
|---|---|
| WS extract (WS-74) (50) + SH (0.5) | 56.69 ± 5.52** |
| Ace Sol/WS-74 (20) + SH (0.5) | 54.24 ± 5.99** |
| Ace Insol/WS-74 (30) + SH (0.5) | 35.48 ± 7.40 |
| IAEF-A (1.0) + SH (0.5) | 65.36 ± 7.38*** |
| Withaferin-A (1) + SH (0.5) | 29.28 ± 9.43 |

Values are Mean ± SEM; n = 8 in each group
P values were obtained by ANOVA followed by post hoc comparison between groups by Newman-Keuls test.
*$p < 0.05$;
**$p < 0.01$;
***$p < 0.001$; in comparison to Scopolamine-treated mice.

TABLE 4

Effect of different treatments on Transfer Latency of Scopolamine-induced amnesic mice on elevated plus maze (After 1 week; i.e., on day 16)

| Treatment Group (mg/kg) | % Decrease in Transfer Latency, Mean ± SEM |
|---|---|
| Vehicle (0.3% CMC) | 57.33 ± 3.63 |
| SH (0.5) | 22.11 ± 5.03 |
| WS extract (WS-74) (50) + SH (0.5) | 62.98 ± 4.34*** |
| Ace Sol/WS-74 (20) + SH (0.5) | 60.80 ± 5.29*** |
| Ace Insol/WS-74 (30) + SH (0.5) | 43.12 ± 7.53 |
| IAEF-A (1.0) + SH (0.5) | 73.49 ± 5.55*** |
| Withaferin-A (1) + SH (0.5) | 34.33 ± 9.30 |

Values are Mean ± SEM; n = 8 in each group
P values were obtained by ANOVA followed by post hoc comparison between groups by Newman-Keuls test.
*$p < 0.05$;
**$p < 0.01$;
***$p < 0.001$; in comparison to Scopolamine-treated mice.

Results of the Scopolamine-induced amnesia experiment are shown in Tables 2-4. Scopolamine hydrobromide produced amnesia in animals as indicated by the increase in the transfer latency on day 9 and day 16 of Group II (Table 2) and attenuated % decrease in TL on day 9 (Table 3) and day 16 (Table 4), in comparison to vehicle-treated Group I (Table 2). WS-74, Ace Sol/WS-74 and IAEF-A significantly attenuated and reversed the Scopolamine-induced amnesia as evidenced by the significant decrease in TL and significant increase in the % decrease of TL, in comparison to Scopolamine-treated group (Group II). Among all the treatment groups, IAEF-A (1 mg/kg) showed the most potent anti-amnesic activity. Ace Insol/WS-74 fraction and Withaferin-A treatments did not protect from or attenuate the Scopolamine-induced amnesia as indicated by the increasing trend in their transfer latency, in comparison to vehicle-treated control group.

Estimation of lipid peroxidation. The animals were sacrificed immediately after the final experiment on day 16 and the brain lipid peroxidation levels were estimated by measuring the brain tissue Malondialdehyde (MDA) concentrations following the published method (H. Ohkawa, et al., "Assay for lipid peroxides in animal tissues by thiobarbituric acid reaction," Anal. Biochem. (1979) 95: 351-358).

Alzheimer's disease (AD) is an irreversible neurodegenerative disorder having symptoms including confusion, memory loss, and mood swings. The beta-amyloid peptide (BAP), with 39-42 amino acid residues, plays a significant role in the development of AD. Although there is no cure for AD, it can be managed with available drugs, but only to a small degree in a small subset of patients. Several studies have revealed that natural antioxidants, such as Vitamin E, Vitamin C and Beta-carotene, may help in scavenging free radicals generated during the initiation and progression of this disease. In this study, the lipid peroxidation levels in brains of different treatment groups were measured by estimating the brain tissue Malondialdehyde (MDA) concentration. The results from the study are presented in Table. 5.

TABLE 5

Effect of different treatments on brain tissue MDA levels in mice with Scopolamine-induced amnesia.

| Treatment Group (mg/kg) | MDA Content, nmol/ml ± SEM |
|---|---|
| Vehicle (0.3% CMC) | 4.75 ± 0.07 |
| SH (0.5) | 5.00 ± 0.10 |
| WS extract (WS-74) (50) + SH (0.5) | 4.73 ± 0.05 |
| Ace Sol/WS-74 (20) + SH (0.5) | 4.60 ± 0.08 |
| Ace Insol/WS-74 (30) + SH (0.5) | 4.97 ± 0.15 |

TABLE 5-continued

Effect of different treatments on brain tissue MDA levels in mice with Scopolamine-induced amnesia.

| Treatment Group (mg/kg) | MDA Content, nmol/ml ± SEM |
|---|---|
| IAEF-A (1.0) + SH (0.5) | 4.32 ± 0.18** |
| Withaferin-A (1) + SH (0.5) | 4.77 ± 0.07 |

Values are Mean ± SEM; n = 4 in each group
P values were obtained by ANOVA followed by post hoc comparison between groups by Newman-Keuls test.
*p < 0.05;
** p < 0.01;
*** p < 0.001; in comparison to Scopolamine-treated mice.

Table 5 indicates that Scopolamine treatment increased the brain tissue MDA levels, and IAEF-A treatment decreased the MDA levels, indicating its antioxidant potential. Other treatments did not show any significant activity.

Referring to the results of the above study, it can be concluded that aqueous extract of WS (WS-74), Ace Sol/WS-74 and IAEF-A showed anti-amnesic activity in the Scopolamine-induced amnesic mice model. Among these test compounds IAEF-A showed the most potent anti-amnesic activity at very low dose (i.e., 1 mg/kg), suggesting that it may be a potential target candidate for Alzheimer's therapy.

Example 4B

Anxiety Paradigms

Anxiety is defined as a feeling of apprehension, uncertainty or tension stemming from the anticipation of imagined or unreal threat. Anxiety affects up to one-eighth of the population worldwide and has become an important research area in the field of psychopharmacology. Benzodiazipines (BZDs), barbiturates, tricyclic antidepressants (TCAs) have been used for a long time in clinical medicine in order to treat anxiety disorders. However, serious side effects associated with these drugs, such as rebound insomnia, sedation, muscle relaxation, withdrawal and development of tolerance (BZDs, barbiturates and alcohol), sexual dysfunction, and anticholinergic and antihistaminic effects (TCAs) have limited their use in patients. Due to such undesirable side effects, there is a continuing quest for alternative medicines or plant derived medications with more specific anxiolytic effects. (S. K. Kulkarni, D. S. Reddy, "Animal behavioural models for testing anti-anxiety agents," *Meth. Find. Exp. Clin. Pharmacol.* (1996) 18: 219-230; and S. K. Kulkarni, et al. "Comparative behavioural profile of newer anti-anxiety drugs on different mazes," *Indian J. Exp. Biol.* (2008) 46:633-638.)

A study was conducted on the anxiolytic effect of WS-74 and its fractions on elevated plus maze and open field exploratory behavior of mice.

Drug Protocol. The animals were divided into 7 groups of six animals in each group. Description of the different groups, dosage and route of administration are presented in Table. 6. Behavioral tests were performed after seven doses maintaining an interval of one hour after last dose.

TABLE 6

| Groups | Treatment | Doses mg/kg, b.w.; route of administration |
|---|---|---|
| Group: I | Vehicle (0.3% CMC) | 0.1 ml/10 g, b.w.; p.o. |
| Group: II | Diazepam | 1.0; p.o. |

TABLE 6-continued

| Groups | Treatment | Doses mg/kg, b.w.; route of administration |
|---|---|---|
| Group: III | WS extract (WS-74) | 50; p.o. |
| Group: IV | Ace Sol/WS-74 | 20; p.o. |
| Group: V | Ace Insol/WS-74 | 30; p.o. |
| Group: VI | IAEF-A | 1; p.o. |
| Group: VII | Withaferin-A (1) | 1; p.o. | n = 6 animals in each group,
b.w. = body weight,
p.o. = oral administration

The doses of different fractions as listed in Table 6, namely, Ace Sol/WS-74, Ace Insol/WS-74, IAEF-A, Withaferin-A, were calculated based on their abundance percentage in the WS extract (WS-74). See also Scheme 1.

Study design. The behavioral tests conducted with multiple seven-dose schedules. The mice were tested only once after the completion of the drug treatment schedule in the elevated plus maze and open field. The studies were carried out in a sound proof room to avoid disturbances to the animals during the behavioral studies. Exposure to a novel environment is associated with emotional disturbance and anxiety. An anxious animal shows reduced ambulation associated with periodic freeze or immobility, and reduction in normal behavior such as rearing and grooming. Anxiety is also associated with augmented autonomic activity resulting in increased defecation and urination. All these effects are accentuated by anxiogenic drugs and attenuated by anxiolytics. Standard screening procedures such as open field method and elevated plus maze test were used to screen the anxiolytic effect of drugs in comparison with a standard drug, Diazepam.

Open-field exploratory behavior test. The open field exploratory apparatus is similar to that of Bronstein (P. M. Bronstein, "Open field behaviour of the rat as a function of age: cross sectional and longitudinal investigations," *J. Comp. Physiol. Psycol.* (1972) 80: 335-341). It is made of plywood and consists of squares (61×61 cm) with high walls. The entire apparatus is painted black except for 6 mm white lines that divide the floor into 16 squares. The entire room except the open field was kept dark during the experiment. The open field was lighted by a 60 W bulb focusing on the field from a height of about 100 cm from the floor. Each animal was centrally placed in the test apparatus for 5 min. and the following behaviors were studied: Ambulation—this measures the number of squares crossed by the animal; Rearings—number of times the animal stands on its hind limbs; Groomings—number of times the animal exhibits grooming of face, licking/washing and scratching the various parts of its body; Fecal pellets—number of fecal pellets excreted during the period; and Activity in center—number of central squares crossed by the animal. The ratio between the number of times the animal crossed the central and the number of times the animal crossed the peripheral square is calculated.

Elevated plus maze (EPM) behavior test. The maze consists of two opposite arms, 50×10 cm, crossed with two opposite enclosed arms of the same dimension with walls 40 cm high. The arms are connected with a central square (10×10 cm) to give the apparatus a plus-sign appearance. The maze was kept elevated 50 cm above the floor in a dimly lit room. The mice were placed individually on the central square of the plus maze facing an enclosed arm. Time spent and the number of entries made by the mice, during the next 5 min. on the open and enclosed arms was recorded. An arm entry was defined when all four limbs of the mice were on the arm (K. C. Montgomery, "The relation between fear induced by novel and exploratory behavior," *J. Comp. Physiol. Psychol.* (1955) 48: 254-60).

Results of the elevated plus maze are presented in Table 7.

TABLE 7

| Treatment Groups | Dose (mg/kg, b.w.) | No. of Entries OA | No. of Entries EA | Time, min. spent on EA |
|---|---|---|---|---|
| Control | — | 8.50 ± 0.56 | 14.17 ± 0.30 | 3.50 ± 0.13 |
| Diazepam | 1 | 9.83 ± 0.07 | 14.50 ± 1.66 | 3.49 ± 0.17 |
| WS extract (WS-74) | 50 | 11.00 ± 0.36 | 14.33 ± 1.11 | 3.68 ± 0.18 |
| Ace Sol/WS-74 | 20 | 10.00 ± 0.44 | 14.67 ± 0.66 | 3.37 ± 0.12 |
| Ace Insol/WS-74 | 30 | 10.00 ± 1.26 | 18.33 ± 0.7* | 4.03 ± 0.21 |
| IAEF-A | 1 | 11.67 ± 1.25* | 9.00 ± 0.63 * | 2.47 ± 0.12 |
| Withaferin-A (1) | 1 | 8.83 ± 0.47 | 15.33 ± 0.98 | 3.86 ± 0.24 |

Values are expressed as Mean ± SEM, n = 6.
OA = Open arm and
EA = Enclosed arm.
P values were obtained by ANOVA followed by post hoc comparison between groups by Newman-Keuls comparison test.
*p < 0.05;
**p < 0.01;
*** p < 0.001; in comparison to vehicle treated mice.

In elevated plus maze behavior, IAEF-A treatment significantly increased the number of open arm entries, open arm residence time and ratio of the open/enclosed arm entries in comparison to control mice (Table.7). IAEF-A treatment also significantly reduced the enclosed arm residence time, indicating an anxiolytic effect. The other treatments did not produce statistically significant anxiolytic effect in mice as evidenced from the data (Table.7). Among the treatment groups, IAEF-A (1 mg/kg) showed more potent anxiolytic activity which is comparable with that of the standard anxiolytic agent, Diazepam.

Results of the open field test are presented in Table 8.

TABLE 8

| Treatment Groups | Dose (mg/kg b.w.) | No. of Ambulations | No. of Rearings | No. of Groomings | No of Fecal Pellets | No. of Times animal crossed Central Square |
|---|---|---|---|---|---|---|
| Control | — | 128.00 ± 1.93 | 36.67 ± 1.60 | 21.17 ± 0.70 | 18.33 ± 0.66 | 4.83 ± 0.30 |
| Diazepam | 1 | 132.20 ± 1.19 | 42.67 ± 1.68 * | 20.33 ± 0.76 | 25.50 ± 0.76 ** | 4.16 ± 0.30 |
| WS extract (WS-74) | 50 | 128.50 ± 2.60 | 32.00 ± 1.31 | 20.67 ± 1.02 | 21.83 ± 2.21 | 4.83 ± 0.16 |
| Ace Sol/WS-74 | 20 | 125.00 ± 2.33 | 29.83 ± 1.97 | 23.50 ± 0.76 | 23.17 ± 1.35 * | 4.50 ± 0.22 |
| Ace Insol/WS-74 | 30 | 121.20 ± 2.60 | 31.50 ± 1.56 | 25.50 ± 0.42 | 31.67 ± 1.08 *** | 5.16 ± 0.30 |
| IAEF-A | 1 | 138.30 ± 3.57 | 40.00 ± 1.39 | 18.83 ± 1.49 | 17.83 ± 1.01 | 3.33 ± 0.21 |
| Withaferin-A (1) | 1 | 108.00 ± 4.46 *** | 26.83 ± 1.77 ** | 26.67 ± 2.23* | 26.67 ± 0.91 *** | 5.16 ± 0.30 |

Values are expressed as Mean ± SEM, n = 6. OA = Open arm and EA = Enclosed arm.
P values were obtained by ANOVA followed by post hoc comparison between groups by Newman-Keuls comparison test.
* p < 0.05;
** p < 0.01;
*** p < 0.001;
in comparison to vehicle treated mice.

As shown in Table 8, IAEF-A treatment produced significant anxiolytic activity in mice as evidenced from increased open field ambulation and rearings, on the one hand, and decreased groomings and fecal pellets on the other, in comparison to control group. However, WS-74, Ace sol/WS-74 and Ace Insol/WS-74 also demonstrated mild anxiolytic effects. Withaferin-A did not show any anxiolytic effect. The anxiolytic effect of the IAEF-A was comparable with that of the Diazepam.

With respect to Example 4B, the elevated plus maze (EPM) behavior test is based on a premise that the exposure to an EPM evoked an approach-avoidance conflict that was considerably stronger than that evoked by the exposure to an enclosed arm. The decrease in aversion to the open arm is the result of an anxiolytic effect, expressed by an increase in the time spent and entries in the open arm. Administration of IAEF-A isolate increased the time spent and percent entries in the open arm, with percent decrease in the closed arm, suggesting the potent anxiolytic activity.

In conclusion, a group of novel indolealkylamino-withasteroid conjugates having Formula (I), isolated and identified from *Withania somnifera* (WS), were found to have potent in vitro acetylcholinesterase inhibitory activity, anti-amnesic activity in scopolamine-induced amnesia mice model and anxiolytic activity in mice. The results suggest that indolealkylamino-withasteroid conjugate(s) (IACs) may be potent target candidate(s) for treating dementia and dementia-related disorders, such as Alzheimer's disease, and anxiety and depressive disorders in mammals.

Example 5

Optimized Extraction of *Withania somnifera* (WS) Fresh Whole Plant by Water

The effect of temperature and duration of extraction were first optimized using water as an extraction solvent. Two sets of macerated fresh whole plant of Ashwagandha (*Withania somnifera*) (20 gm each) were suspended in water (120 ml), in separate vessels. One set was extracted at 80±5° C. on a steam bath and another set was extracted at 100±5° C. using a heating mantle. Extracted samples at different time intervals (0 Hr, 1 Hr, 2 Hr, 3 Hr, 4 Hr, 5 Hr, 6 Hr, 8 Hr, 10 Hr and 12 Hr) were collected and filtered and the filtrates were directly injected into an HPLC apparatus. Filtrates (3 ml) collected at each time interval were dried on the steam bath, and the weight of each residue was taken to determine the concentration of the extractives, as shown in Tables 9 and 10. The average yield of all of the dried extractives was 3.17 g at 80±5° C., and 4.46 g at 100±5° C. In the following Tables, the amounts of WG, AG, and IAC were determined as described above in the HPLC analytical method.

TABLE 9

Amounts of bioactives of hot (80 ± 5° C.) aqueous extract of fresh whole plant of WS at different time intervals.

| Time interval | Withanolide glycosides (WG) (%) | Aglycons (AG) (%) | Total (WG + AG) (%) | Indolealkylamino-Withasteroid conjugates (%) |
|---|---|---|---|---|
| 0 hr* | 4.10 | 3.83 | 7.93 | 1.04 |
| 1 hr | 5.40 | 2.11 | 7.51 | 1.22 |
| 2 hr | 6.40 | 1.94 | 8.34 | 0.85 |
| 3 hr | 7.73 | 1.65 | 9.39 | 1.56 |
| 4 hr | 7.07 | 1.66 | 8.73 | 0.75 |
| 5 hr | 6.39 | 1.35 | 7.74 | 1.11 |
| 6 hr | 3.53 | 1.59 | 5.11 | 0.83 |
| 8 hr | 3.17 | 1.46 | 4.63 | 1.12 |
| 10 hr | 3.00 | 1.44 | 4.44 | 0.84 |
| 12 hr | 1.01 | 1.08 | 2.09 | 0.55 |

*indicates instant extraction
% = wt. % based on WS dry extract

TABLE 10

Amounts of bioactives of hot (100 ± 5° C.) aqueous extract of fresh whole plant of WS at different time intervals.

| Time interval | Withanolide glycosides (WG) (%) | Aglycons (AG) (%) | Total (WG + AG) (%) | Indolealkylamino-Withasteroid conjugates (%) |
|---|---|---|---|---|
| 0 hr* | 4.10 | 3.83 | 7.93 | 1.04 |
| 1 hr | 7.40 | 1.91 | 9.31 | 1.54 |
| 2 hr | 6.86 | 2.30 | 9.16 | 1.44 |
| 3 hr | 6.51 | 1.71 | 8.22 | 1.45 |
| 4 hr | 5.69 | 1.68 | 7.38 | 1.17 |
| 5 hr | 5.76 | 1.65 | 7.41 | 0.75 |
| 6 hr | 3.97 | 1.65 | 5.62 | 1.44 |
| 8 hr | 1.62 | 1.15 | 2.78 | 0.75 |
| 10 hr | 1.54 | 0.93 | 2.47 | 0.74 |
| 12 hr | 1.56 | 0.93 | 2.50 | 1.14 |

*indicates instant extraction

As shown in Tables 9 and 10, hot water extraction of WS demonstrated that total withanolide (WG+AG) and indole-alkylamino-withasteroid conjugates (IACs) were extracted more efficiently at 80±5° C. and 100±5° C. in a time range up to about 3 hours to 4 hours. Maximum concentrations of both total withanolide (WG+AG) and indolealkylamino-withasteroid conjugates (IACs) were observed at 80±5° C. at 3 hours. Duration of hot water extraction beyond about 3 hours resulted in both a lower extraction yield, and reduced potency in the extractives.

Example 6

Optimized Extraction of *Withania somnifera* (WS) Fresh Whole Plant by Aqueous Methanol The effect of temperature and duration of extraction were optimized using a mixed solvent extraction. Two sets of macerated fresh whole plant of Ashwagandha (*Withania somnifera*) (20 gm each) were suspended in aqueous-methanol (water:MeOH 40:60 v/v, 120 ml), in separate vessels. One set was extracted at 80±5° C. on a steam bath and another set was extracted at 100±5° C. using a heating mantle and using a cold water-cooled reflux condenser. Extracted samples at different time intervals (0 Hr, 1 Hr, 2 Hr, 3 Hr, 4 Hr, 5 Hr, 6 Hr, 8 Hr, 10 Hr and 12 Hr) were collected, filtered and the filtrates directly injected into an HPLC apparatus. Filtrates (3 ml) collected at each time interval were dried on the steam bath, and the weight of each residue was taken to determine the concentration of the extractives, as shown in Tables 11 and 12. The average yield of all of the dried extractives was 4.28 g at 80±5° C., and 4.92 g at 100±5° C.

TABLE 11

Amounts of bioactives of hot (80 ± 5° C.) Aqueous-methanol extract fresh whole plant of WS in different time intervals.

| Time interval | Withanolide glycosides (WG) (%) | Aglycons (AG) (%) | Total (WG + AG) (%) | Indolealkylamino-Withasteroid conjugates (%) |
|---|---|---|---|---|
| 0 hr* | 7.09 | 4.51 | 11.59 | 1.35 |
| 1 hr | 4.90 | 5.95 | 10.85 | 1.65 |
| 2 hr | 6.05 | 5.40 | 11.45 | 1.51 |
| 3 hr | 6.93 | 5.30 | 12.23 | 1.46 |
| 4 hr | 6.26 | 5.22 | 11.49 | 1.34 |
| 5 hr | 4.83 | 4.82 | 9.66 | 1.36 |
| 6 hr | 3.32 | 5.10 | 8.41 | 1.09 |
| 8 hr | 3.11 | 4.83 | 7.94 | 1.18 |
| 10 hr | 3.24 | 4.27 | 7.51 | 1.13 |
| 12 hr | 2.49 | 4.43 | 6.92 | 1.05 |

*indicates instant extraction
% = wt. % based on WS dry extract

TABLE 12

Amounts of bioactives of hot (100 ± 5° C.) Aqueous-methanol extract fresh whole plant of WS in different time intervals.

| Time interval | Withanolide glycosides (WG) (%) | Aglycons (AG) (%) | Total (WG + AG) (%) | Indolealkylamino-Withasteroid conjugates (%) |
|---|---|---|---|---|
| 0 hr* | 7.09 | 4.51 | 11.59 | 1.35 |
| 1 hr | 8.37 | 5.83 | 14.19 | 2.33 |
| 2 hr | 6.15 | 3.92 | 10.07 | 1.55 |
| 3 hr | 5.40 | 4.30 | 9.70 | 1.50 |
| 4 hr | 5.64 | 3.80 | 9.44 | 1.47 |
| 5 hr | 4.58 | 4.59 | 9.17 | 1.22 |
| 6 hr | 4.46 | 3.74 | 8.20 | 1.14 |
| 8 hr | 4.04 | 4.41 | 8.45 | 1.02 |
| 10 hr | 3.16 | 4.30 | 7.46 | 0.96 |
| 12 hr | 2.94 | 4.27 | 7.21 | 0.86 |

*indicates instant extraction

As shown in Tables 11 and 12, hot mixed solvent extraction of WS demonstrated that although significant amounts of bioactives were observed at 80±5° C., maximum concentrations of both total withanolide (WG+AG) and indolealkylamino-withasteroid conjugates (IACs) were observed at 100±5° C. at 1 hour. Longer extraction times did not appear to be as effective for the mixed solvent experiments at 100±5° C.

Based on experiments performed in Examples 5 and 6, it appears that hot water extraction of WS at 80±5° C. for 3 hours is an optimal condition in order to achieve maximum concentrations of both total withanolide (WG+AG) and indolealkylamino-withasteroid conjugates (IACs). Under the optimized conditions used, weight percent yields of IACs were shown to range from about 0.75% to about 1.6%. It is expected that weight percent yields of IACs could be further improved by varying the extraction parameters in accordance with the principles of the present invention.

It is further expected that an IAC and/or withanolide-enriched WS extract made in accordance with the principles of the invention would be effective as a nutritional supplement. It is further expected that a WS extract or a composition containing an IAC, namely, a compound of Formula (I), or a derivative thereof, would be effective as a nutritional supplement.

It is further expected that a WS extract or a composition containing an IAC, namely, a compound of Formula (I), or a derivative thereof, would be effective in a pharmaceutical composition or a nutraceutical composition, when in combination with an appropriate pharmaceutical or nutraceutical carrier or excipient, respectively. Said pharmaceutical compositions would be effective for treating neurodegenerative disorders, such as, Alzheimer's disease (AD), or psychiatric disorders, such as, anxiety or depression. Said nutraceutical compositions would be effective for supplementing nutrition and/or health, thus providing increased health benefits to the user.

Example 7

The cognition-facilitating effects of the tryptamino-withaferin-A conjugates having Formula (I) were assessed by the following pharmacological screening experiments.

Example 7A

Pharmacological Activity of Conjugates of Formula (I): In Vitro Inhibition of Acetylcholine-Esterase Activity The tryptamino-withaferin-A conjugate (Ex. 1A.3) and 5-methoxytryptamino-withaferin-A conjugate (Ex. 2A), prepared synthetically over a solid alumina support, were subjected to in vitro acetylcholinesterse activity assay to determine their anti-cholinesterase activity. The acetylcholinesterase (AChE) assay was performed by the method of Ellman et. al., with minor modification, using acetylthiocholine Iodide as a substrate (G. L. Ellman, et al., "A new and rapid colorimetric determination of acetylcholinesterase activity," *Biochem. Pharmacol.* (1961) 7: 88-95). Ellman's reaction mixture was made from a combination of 10 mM Acetylthiocholine iodide and 0.5 mM 5,5'-dithio-bis-(2-nitrobenzoic acid) in a 0.05 M sodium phosphate buffer (pH 7.2). The rates of hydrolysis by AChE were monitored spectrophotometrically using a 96-well microtiter plate reader. Each test sample (10 μl) and 0.05 M sodium phosphate buffer (30 μl) was mixed with the enzyme solution (10 μl). An Ellman's reaction mixture (50 μl) was further added to give a final volume of 100 μl, and the mixture was incubated at 37° C. for 30 min. Absorbance at 450 nm was recorded immediately after adding the Ellman's reaction mixture. Reading was repeated for 10 min at 2 min intervals to verify that the reaction occurred linearly. Blank reaction was measured by substituting saline for the enzyme (Y. K. Chung, et al., "Inhibitory effect of ursolic acid purified from *Origanum majorana* L. on the acetylcholinesterase," Mol. Cells (2001) 11: 137-143).

The tryptamino-withaferin-A conjugate (Ex. 1A.3) and 5-methoxytryptamino-withaferin-A conjugate (Ex. 2A) were tested as described above to afford acetylcholinesterase inhibition data and $IC_{50}$'s. The results indicated that tryptamino-withaferin-A conjugate and 5-methoxytryptamino-withaferin-A conjugate exhibited good dose-dependent in-vitro acetylcholinesterase inhibitory activity. The IC50 values are incorporated in Table 13.

TABLE 13

In vitro acetylcholinesterase inhibitory activity of tryptamino-withaferin-A conjugate and 5-methoxytryptamino-withaferin-A conjugate.

| Test substance | Acetylcholinesterase inhihitory activity $IC_{50}$ (μg/ml) |
|---|---|
| Tryptamino-withaferin-A conjugate (Ex. 1A.3) | 35.40 ± 4.44 |
| 5-Methoxytryptamino-withaferin-A conjugate (Ex. 2A) | 98.76 ± 8.46 |

Values are represented as Mean ± SD of three replicates

The IC50 values in Table 13 indicate that both conjugates have appreciable acetylcholinesterase inhibitory. However, tryptamino-withaferin-A conjugate exhibited better acetylcholinesterase inhibitory activity than 5-methoxytryptamino-withaferin-A conjugate.

Example 7B

Effect of Tryptamino-Withaferin-A Conjugate and 5-Methoxytryptamino-Withaferin-A Conjugate on Scopalamine-Induced Amnesia and Anxiety Paradigms In Vivo Experimental animals. Swiss Albino mice of both sexes weighing approximately 24±4 g, 6-7 weeks old were obtained from National Research Institute of *Ayurveda* for Drug Development (Govt. of India), Kolkata, and were housed in polypropylene cages at 22±3° C. and relative air humidity of 45-55%, with 12.00 hour light & dark cycle (lighting on from 6:00 AM to 6:00 PM). Mice were provided a standard pellet chow (carbohydrate 65.5%, protein 17.6%, fat 6.6%) and distilled water ad libitum. The mice were acclimatized for one week in the laboratory conditions, before being used in the experiment. All experiments were conducted between 10:00 AM and 2:00 PM. Principles of laboratory animal care (NIH publication no. 85-23, revised 1985) were always followed.

Drug preparation and administration of doses. Test samples were suspended in 0.3% Carboxymethyl Cellulose (CMC) solutions of distilled water and were administered orally for 16 days by using an intubation canula, and volume of dose was 0.1 ml/10 g body weight. The tryptamino-withaferin-A conjugate (Ex. 1A.3) and 5-methoxytryptamino-withaferin-A conjugate (Ex. 2A) were administered orally for 16 days in 0.3% CMC solution. The experiments were carried out after 45 minutes of the administration of the drugs. Control animals received equivalent volume of the vehicle, 0.3% CMC solution, only.

Scopolamine-Induced Amnesia. Alzheimer's disease is associated with significant losses in cholinergic neurons and decreased concentrations of the neurotransmitter, acetylcholine, which is significantly involved in learning and memory processes. Scopolamine hydrobromide produces amnesia in mice because of its anti-cholinergic action. Scopolamine hydrobromide exerts its effects by acting as a competitive antagonist at muscarinic acetylcholine receptors, specifically M1 receptors. Because of its anti-cholinergic effects, scopolamine hydrobromide has been shown to prevent the activation of medial temporal lobe structures for novel stimuli during spatial memory tasks. It has also been shown to impair memory in humans in a manner mimicking the cognitive deficits found in Alzheimer's Dementia. Therefore, in the present study, a scopolamine hydrobromide-induced amnesic model using elevated plus maze was selected to evaluate the anti-amnesic effects of tryptamino-withaferin-A conjugate (Ex. 1A.3) and 5-methoxytryptamino-withaferin-A conjugate (Ex. 2A). The elevated plus maze is used to measure the memory learning activity in mice; however, transfer latency, i.e., the time elapsed between the movement of the animal from an open to an enclosed arm was markedly shortened if the animal had previously experienced entering open and closed arms.

Amnesia was induced by administration of scopolamine hydrobromide (0.5 mg/kg, i.p.) on the $8^{th}$ day immediately after the learning trial. Retention was recorded after 24 hrs ($9^{th}$ day) and after an interval of one week ($16^{th}$ day).

Drug protocol. The animals were divided into 6 groups (Group I-VI) of eight animals in each group. Group I received vehicle (0.3% CMC) only and served as vehicle control. Groups II-VI were treated with the respective test drugs, as per the details mentioned in Table 14 below, for 16 days. Scopolamine hydrobromide (0.5 mg/kg, i.p.) was administered to groups II-VI on the $8^{th}$ day immediately after the learning trial. Transfer Latency was recorded after 45 minutes of the drug administration on $8^{th}$ day (learning trial) and 24 hrs ($9^{th}$ day) and one week ($16^{th}$ day) after learning trial.

TABLE 14

| Groups | Treatment | Doses mg/kg, b.w.; route of administration |
|---|---|---|
| I | Vehicle (0.3% CMC) | 0.1 ml/10 g, b.w.; p.o. |
| II | SH | 0.5 ; i.p. |
| III | Tryptamino-withaferin-A conjugate + SH | 1; p.o. + 0.5; i.p. |
| IV | Tryptamino-withaferin-A conjugate + SH | 5; p.o. + 0.5; i.p. |
| V | 5-Methoxytryptamino-withaferin-A conjugate + SH | 1; p.o. + 0.5; i.p. |
| VI | 5-Methoxytryptamino-withaferin-A conjugate + SH | 5; p.o. + 0.5; i.p. | n = 8 animals in each group,
b.w. = body weight,
SH = Scopolamine Hydrobromide,
p.o. = oral administration,
i.p. = intraperitoneal administration.

Retention in elevated plus maze test was used to assess the memory functions in test animals. The plus maze consists of two open opposite arms, (50×10 cm) length×width, crossed with two enclosed arms of same dimensions with walls 40 cm high. The arms are connected with a central square, (10×10 cm) to give the apparatus a plus-sign appearance. The maze was kept elevated 50 cm above the floor in a dimly lit room. On day 8, mice were individually placed on far end of one of the open arms facing away from the center and transfer latency (TL) on day 8 was recorded. TL is the time taken by the mouse to move into any one of the covered arms with all its four legs. The mice were left in the enclosed arms for 10-15 s and then were taken to the home cage. On day 9, the mice were again placed on the far end of the open arm and time taken by the mice to enter the enclosed arm, transfer latency (TL) day 9, was recorded. Similarly after an interval of one week, on day 16, the transfer latency (TL) day 16 was again recorded. (J. Itoh, et al., "Utility of an elevated plus maze for the evaluation of nootropics, scopolamine and electro convulsive shock," *Psychopharmacol.* (1990): 101:27-33; M. Parle, et al., "Improvement of mouse memory by *Myristica fragrans* seeds," *J Med. Food.* (2004) 7:157-61; and H. Joshi, et al., "Brahmirasayana Improves Learning and Memory in Mice," *eCAM* (2006) 3: 79-85.)

The retention scores were obtained for each animal by calculating percent decrease in latency period by the formula:

$$\% \text{ decrease in } TL = (L_1 - L_0/L_0) \times 100 \quad \text{Equation (1)}$$

where, $L_0$=initial transfer latency period in seconds, and $L_1$=transfer latency after 24 hrs or one week.

Results of the Scopolamine-induced amnesia experiment are presented in Tables 15-17 following.

TABLE 15

Effect of different treatments on Transfer Latency of Scopolamine-induced amnesic mice on elevated plus maze

| Treatment Group (mg/kg) | Transfer Latency (s) | | |
|---|---|---|---|
| | Day 8 | Day 9 | Day 16 |
| Vehicle (0.3% CMC) | 173.20 ± 97.77 | 59.17 ± 19.66 | 19.00 ± 11.58 |
| SH (0.5) | 160.00 ± 66.68 | 106.00 ± 42.81$^{aa}$ | 48.17 ± 12.73$^{aaa}$ |
| Tryptamino-withaferin-A conjugate (1) + SH(0.5) | 178.00 ± 117.90 | 56.17 ± 21.99$^{b}$ | 16.50 ± 9.52$^{bbb}$ |
| Tryptamino-withaferin-A conjugate (5) + SH (0.5) | 159.00 ± 126.20 | 51.67 ± 15.28 $^{b}$ | 15.17 ± 10.09$^{bbb}$ |
| 5-methoxytryptamino-withaferin-A conjugate (1) + SH(0.5) | 139.1 ± 25.05 | 76.63 ± 33.95 | 43.13 ± 12.43 |
| 5-methoxytryptamino-withaferin-A conjugate (5) + SH (0.5) | 141.00 ± 35.66 | 37.25 ± 4.43$^{bb}$ | 18.00 ± 4.14$^{bbb}$ |

SH = Scopolamine Hydrobromide
Values were expressed in mean ± SD (n = 8).
P values were obtained by ANOVA followed by post hoc comparison between groups by Newman-Keuls test.
$^{a}$p < 0.05;
$^{aa}$p < 0.01;
$^{aaa}$p < 0.001; in comparison to vehicle treatment after 24 hrs.
$^{b}$p < 0.05;
$^{bb}$p < 0.01;
$^{bbb}$p < 0.001; in comparison to SH treatment after one week.

TABLE 16

Effect of different treatments on Transfer Latency of Scopolamine-induced amnesic mice on elevated plus maze (After 24 h; i.e., on day 9)

| Treatment Group (mg/kg) | % Decrease in Transfer Latency, Mean ± SD |
|---|---|
| Vehicle (0.3% CMC) | 54.83 ± 29.79 |
| SH (0.5) | 29.86 ± 17.79 |
| Tryptamino-withaferin-A conjugate (1) + SH(0.5) | 54.97 ± 27.54 |
| Tryptamino-withaferin-A conjugate (5) + SH (0.5) | 59.93 ± 13.31 |
| 5-methoxytryptamino-withaferin-A conjugate (1) + SH(0.5) | 45.62 ± 16.51 |
| 5-methoxytryptamino-withaferin-A conjugate (5) + SH(0.5) | 72.18 ± 6.60. |

Values are Mean ± SD;
n = 8 in each group
P values were obtained by ANOVA followed by post hoc comparison between groups by Newman-Keuls test.
*p < 0.05;
**p < 0.01;
***p < 0.001; in comparison to Scopolamine-treated mice.

TABLE 17

Effect of different treatments on Transfer Latency of Scopolamine-induced amnesic mice on elevated plus maze (After 1 week; i.e., on day 16)

| Treatment Group (mg/kg) | % Decrease in Transfer Latency, Mean ± SEM |
|---|---|
| Vehicle (0.3% CMC) | 86.47 ± 6.96 |
| SH (0.5) | 63.54 ± 18.87$^{aa}$ |
| Tryptamino-withaferin-A conjugate (1) + SH(0.5) | 88.10 ± 6.17$^{b}$ |
| Tryptamino-withaferin-A conjugate (5) + SH (0.5) | 85.72 ± 11.96$^{bb}$ |
| 5-methoxytryptamino-withaferin-A conjugate (1) + SH(0.5) | 69.13 ± 5.38 |
| 5-methoxytryptamino-withaferin-A conjugate (5) + SH(0.5) | 85.79 ± 9.92$^{bb}$ |

Values are Mean ± SD;
n = 8 in each group
P values were obtained by ANOVA followed by post hoc comparison between groups by Newman-Keuls test.
*p < 0.05;
**p < 0.01;
***p < 0.001; in comparison to Scopolamine-treated mice.

Results of the Scopolamine-induced amnesia experiment are shown in Tables 15-17. Scopolamine hydrobromide produced amnesia in animals as indicated by the increase in the transfer latency on day 9 and day 16 of Group II (Table 15) and attenuated % decrease in TL on day 9 (Table 16) and day 16 (Table 17), in comparison to vehicle-treated Group I. Tryptamino-withaferin-A conjugate (Ex. 1A.3) and 5-methoxytryptamino-withaferin-A conjugate (Ex. 2A) significantly attenuated and reversed the Scopolamine-induced amnesia as evidenced by the significant decrease in TL and significant increase in the % decrease of TL, in comparison to Scopolamine-treated group (Group II). Both the conjugates exhibited equi-potent anti-amnesic activity in the scopolamine-induced amnesia in mice.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of treating Alzheimer's disease in an individual, comprising administering to the individual in need of such treatment a therapeutically effective amount of a compound of Formula (I), or a pharmaceutically acceptable salt thereof:

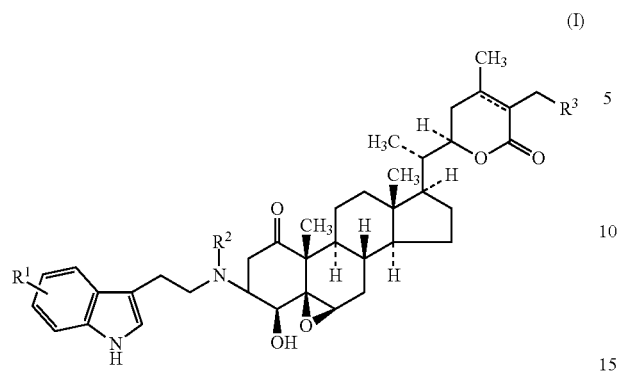

(I)

wherein R¹ is selected from the group consisting of hydrogen, ($C_1$-$C_3$)-alkyl, hydroxyl, and ($C_1$-$C_4$)-alkoxy;

wherein R² is hydrogen or ($C_1$-$C_3$)-alkyl;

wherein R³ is hydrogen or hydroxyl; and wherein ------ represents a single or a double bond.

2. The method of claim 1, wherein the compound is effective to inhibit acetylcholinesterase activity.

3. A method of treating an anxiety disorder in an individual, comprising administering to the individual in need of such treatment a therapeutically effective amount of a compound of Formula (I), or a pharmaceutically acceptable salt thereof:

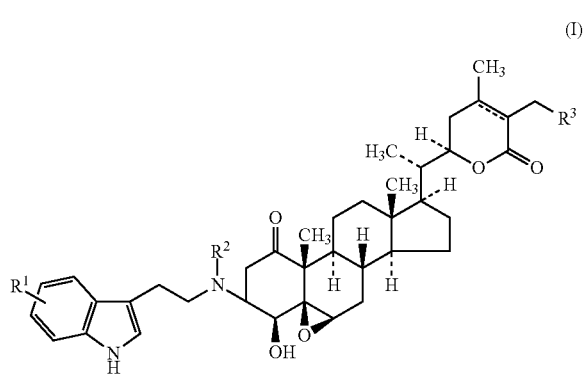

(I)

wherein R¹ is selected from the group consisting of hydrogen, ($C_1$-$C_3$)-alkyl, hydroxyl, and ($C_1$-$C_4$)-alkoxy;

wherein R² is hydrogen or ($C_1$-$C_3$)-alkyl;

wherein R³ is hydrogen or hydroxyl; and wherein ------ represents a single or a double bond.

4. The method of claim 3, wherein the compound is effective to inhibit acetylcholinesterase activity.

\* \* \* \* \*